US007871786B2

(12) United States Patent
Smeal et al.

(10) Patent No.: US 7,871,786 B2
(45) Date of Patent: Jan. 18, 2011

(54) GEF-H1B: BIOMARKERS, COMPLEXES, ASSAYS AND THERAPEUTIC USES THEREOF

(75) Inventors: Tod R. Smeal, San Francisco, CA (US); Marinella G. Callow, San Mateo, CA (US); Bahija Jallal, Menlo Park, CA (US); Sergey Zozulya, Los Angeles, CA (US); Mikhail L. Gishizky, Menlo Park, CA (US)

(73) Assignee: Sugen, Inc., New York, NY (US)

( * ) Notice: Subject to any disclaimer, the term of this patent is extended or adjusted under 35 U.S.C. 154(b) by 0 days.

(21) Appl. No.: 12/232,134

(22) Filed: Sep. 11, 2008

(65) Prior Publication Data

US 2009/0130695 A1   May 21, 2009

Related U.S. Application Data

(62) Division of application No. 10/611,671, filed on Jul. 2, 2003, now Pat. No. 7,439,329.

(60) Provisional application No. 60/393,600, filed on Jul. 5, 2002, provisional application No. 60/460,053, filed on Apr. 4, 2003.

(51) Int. Cl.
*G01N 33/53* (2006.01)
*A61K 39/395* (2006.01)
*C07K 16/00* (2006.01)
*C07K 5/00* (2006.01)

(52) U.S. Cl. .................. 435/7.1; 435/7.2; 435/7.21; 435/7.23; 424/139.1; 424/158.1; 530/387.1; 530/387.9; 530/300; 530/340

(58) Field of Classification Search .................. None
See application file for complete search history.

(56) References Cited

U.S. PATENT DOCUMENTS

| | | | |
|---|---|---|---|
| 5,863,532 A | 1/1999 | Traugh et al. | |
| 2005/0100554 A1 | 5/2005 | Jackson et al. | |

FOREIGN PATENT DOCUMENTS

| | | |
|---|---|---|
| DE | 44 12 174 | 10/1995 |
| WO | WO 88/06598 | 9/1988 |
| WO | WO 99/53036 | 10/1999 |
| WO | WO 99/63073 | 12/1999 |
| WO | WO 01/32687 | 5/2001 |

OTHER PUBLICATIONS

Callow et al., J. Biol. Chem., Jan. 2002, vol. 277(1):550-558.*
Zenke et al., J. Biol. Chem., 2004, vol. 279(18):18392-18400.*
Abo et al., "PAK4, a novel effector for Cdc42Hs, is implicated in the reorganization of the actin cytoskeleton and in the formation of filopodia," *The EMBO Journal*, 1998, pp. 6527-6540, vol. 17, No. 22, Oxford University Press.
Callow et al., "Requirement for PAK4 in the Anchorage-independent Growth of Human Cancer Cell Lines," *The Journal of Biological Chemistry*, Jan. 4, 2002, pp. 550-558, vol. 277, No. 1, The American Society for Biochemistry and Molecular Biology, Inc., USA.
Chan et al., "Expression cDNA cloning of a novel oncogene with sequence similarity to regulators of small GTP-binding proteins," *Oncogene*, 1994, pp. 1057-1063, vol. 9, Macmillan Press Ltd.
Cravchik et al., "A novel strategy for the immunological tagging of cDNA constructs," *Gene*, 1993, pp. 139-143, vol. 137, Elsevier Science Publishers B.V.
Dan et al., "Cytoskeletal Changes Regulated by the PAK4 Serine/Threonine Kinase Are Mediated by LIM Kinase 1 and Cofilin," *The Journal of Biological Chemistry*, Aug. 24, 2001, pp. 32115-32121, vol. 276, No. 34, The American Society for Biochemistry and Molecular Biology, Inc., USA.
Dan et al., "PAK5, a New Brain-Specific Kinase, Promotes Neurite Outgrowth in N1E-115 Cells," *Molecular and Cellular Biology*, Jan. 2002, pp. 567-577, vol. 22, No. 2, American Society for Microbiology.
Deo et al., "Green Fluorescent Protein Mutant as Label in Homogeneous Assays for Biomolecules," *Analytical Biochemistry*, 2001, pp. 52-59, vol. 289, Academic Press.
Gauthier-Rouvière et al., "*ras*-induced c-*fos* expression and proliferation in living rat fibroblasts involves C-kinase activation and the serum response element pathway," *The EMBO Journal*, 1990, pp. 171-180, vol. 9, No. 1, Oxford University Press.
Gnesutta et al., "The Serine/Threonine Kinase PAK4 Prevents Caspase Activation and Protects Cells from Apoptosis," *The Journal of Biological Chemistry*, Apr. 27, 2001, pp. 14414-14419, vol. 276, No. 17, The American Society for Biochemistry and Molecular Biology, Inc., USA.
Hashimura et al., "Production of Rabbit Antibody Specific for Amino-Terminal Residues of Cholecystokinin Octapeptide (CCK-8) by Selective Suppression of Cross-Reactive Antibody Response," *Journal of Immunological Methods*, 1982, pp. 375-387, vol. 55, Elsevier Biomedical Press.
Krendel et al., "Nucleotide exchange factor GEF-H1 mediates crosstalk between microtubules and the actin cytoskeleton," *Nature Cell Biology*, Apr. 2002, pp. 294-301, vol. 4, No. 4.
Musacchio et al., "The PH domain: a common piece in the structural patchwork of signaling proteins," *Trends in Biochemical Sciences*, Sep. 1993, pp. 343-348, vol. 18, The International Union of Biochemistry and Molecular Biology and Elsevier Trends Journals.

(Continued)

*Primary Examiner*—Elizabeth C. Kemmerer
*Assistant Examiner*—Xiaozhen Xie
(74) *Attorney, Agent, or Firm*—Austin W. Zhang; Jeffrey H. Tidwell

(57) ABSTRACT

The present invention relates to diagnosing abnormal cell proliferation in biological samples and screening for drugs which inhibit, reduce or abolish cell growth, especially tumorigenic cell growth, by detecting a phosphovariant isoform of a guanine nucleotide exchange factor biomarker, such as the novel GEF-H1S.

6 Claims, 12 Drawing Sheets

OTHER PUBLICATIONS

Nims et al., "Production of Hyperimmune Serum With Mature Rabbits," *Laboratory Animal Science*, 1973, pp. 391-396, vol. 23, No. 3, American Association for Laboratory Animal Science, USA.

Nobes et al., "Rho, rac and cdc42 GTPases: regulators of actin structures, cell adhesion and motility," *Biochemical Society Transactions*, 654th Meeting Leicester, Aug. 1995, pp. 456-459, vol. 23, No. 3.

O'Shea et al., "The ins and outs of cell-polarity decisions," *Nature Cell Biology*, Mar. 2000, pp. E39-E41, vol. 2, No. 3.

Pandey et al., "Cloning and Characterization of PAK 5, a novel member of mammalian p21-activated kinase-II subfamily that is predominantly expressed in brain," *Oncogene*, 2002, pp. 3939-3948, vol. 21, Nature Publishing Group.

Qu et al., "Activated PAK4 Regulates Cell Adhesion and Anchorage-Independent Growth," *Molecular and Cellular Biology*, May 2001, pp. 3523-3533, vol. 21, No. 10, American Society for Microbiology.

Reddy et al., "Isolation and Characterization of Complementary DNA to Proliferating Cell Nucleolar Antigen P40," *Cancer Research*, Apr. 1, 1989, pp. 1763-1767, vol. 49, No. 7, American Association for Cancer Research.

Ren et al., "Cloning and Characterization of GEF-H1, a Microtubule-associated Guanine Nucleotide Exchange Factor for Rac and Tho GTPases," *The Journal of Biological Chemistry*, Dec. 25, 1998, pp. 34954-34960, vol. 273, No. 52, The American Society for Biochemistry and Molecular Biology, Inc.

Sato et al., "Fluorescent indicators for imaging protein phosphorylation in single living cells," *Nature Biotechnology*, Mar. 2002, pp. 287-294, vol. 20, No. 3.

Shamah et al., "EphA Receptors Regulate Growth Cone Dynamics through the Novel Guanine Nucleotide Exchange Factor Ephexin," *Cell*, Apr. 20, 2001, pp. 233-244, vol. 105, Cell Press.

Taylor et al., "Nonradioactive Determination of Ras-GTP levels Using Activated Ras Interaction Assay," *Methods in Enzymology*, 2001, pp. 333-342, vol. 333, Academic Press.

Yang et al., "Androgen Receptor Specifically with a Novel p21-activated Kinase, PAK6," *The Journal of Biological Chemistry*, May 4, 2001, pp. 15345-15353, vol. 276, No. 18, The American Society for Biochemistry and Molecular Biology, Inc., USA.

Zozulya et al., "Mapping signal transduction pathways by phage display," *Nature Biotechnology*, Dec. 1999, pp. 1193-1198, vol. 17, Nature America Inc.

Ren et al., "Cloning and characterization of GEF-H1, a microtubule-associated guanine nucleotide exchange for Rac and Rho GTPases," *J. Biol. Chem.*, Dec. 25, 1998, pp. 34954-34960, vol. 273, No. 5.

Whitehead et al., "Expression cloning of lfc, a novel oncogene with structural similarities to guanine nucleotide exchange factors and to the regulatory region of protein kinase C," *J. Biol. Chem.*, Aug. 4, 1995, pp. 18388-18395, vol. 275, No. 31.

*Lexikon der Biochemie und Molekularbiologie*, 1991, pp. 65-69, Herder Verlag.

Scacco et al., J. Biol. Chem., 2000, vol. 275(23), pp. 17578-17582.

Krendel et al., Nature Cell Biol., 2002, 4, pp. 294-301.

Ren et al., J. Biol. Chem., 1998, vol. 273(52), pp. 34954-34960.

Callow et al., "PAK4 Mediates Morphological Changes Through the Regulation of GEF-H1," Journal of Cell Science, vol. 118, No. Pt. 9, pp. 1861-1872 (2005).

* cited by examiner

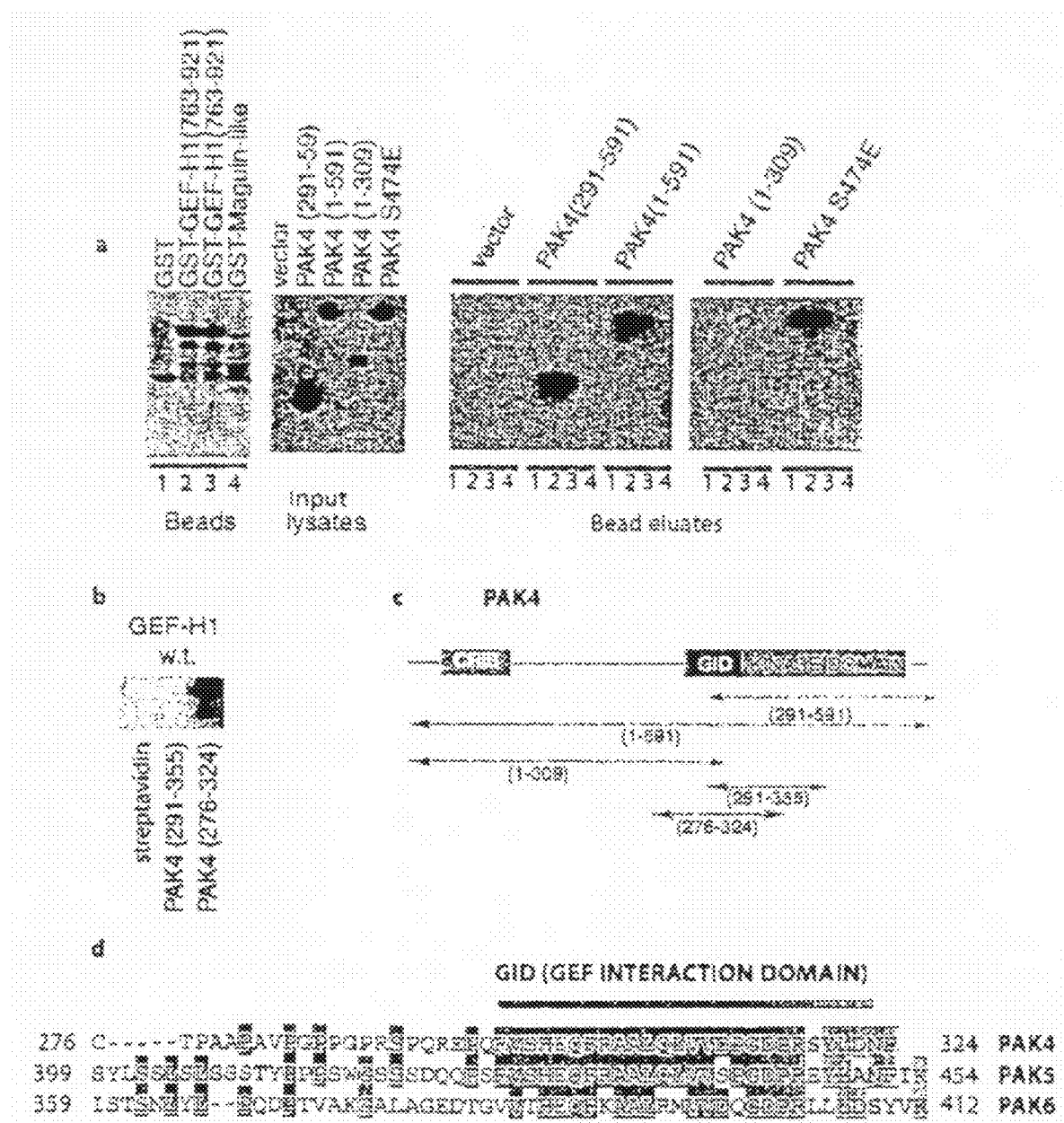
Fig 1. In vitro association of GEF-H1 with PAK4 alleles and subdomains.

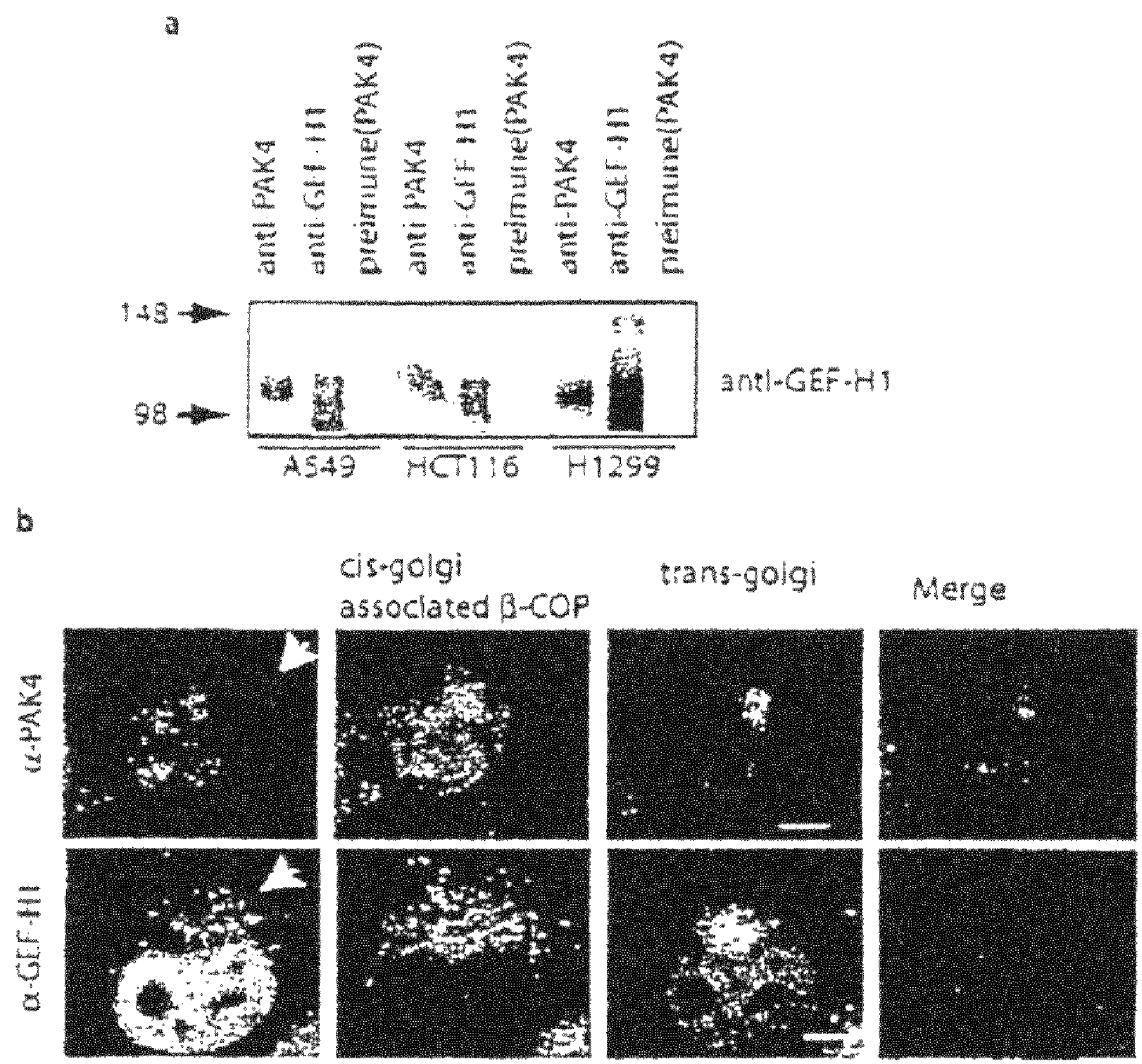
Fig 2. PAK4 and GEF-H1 co-associate.

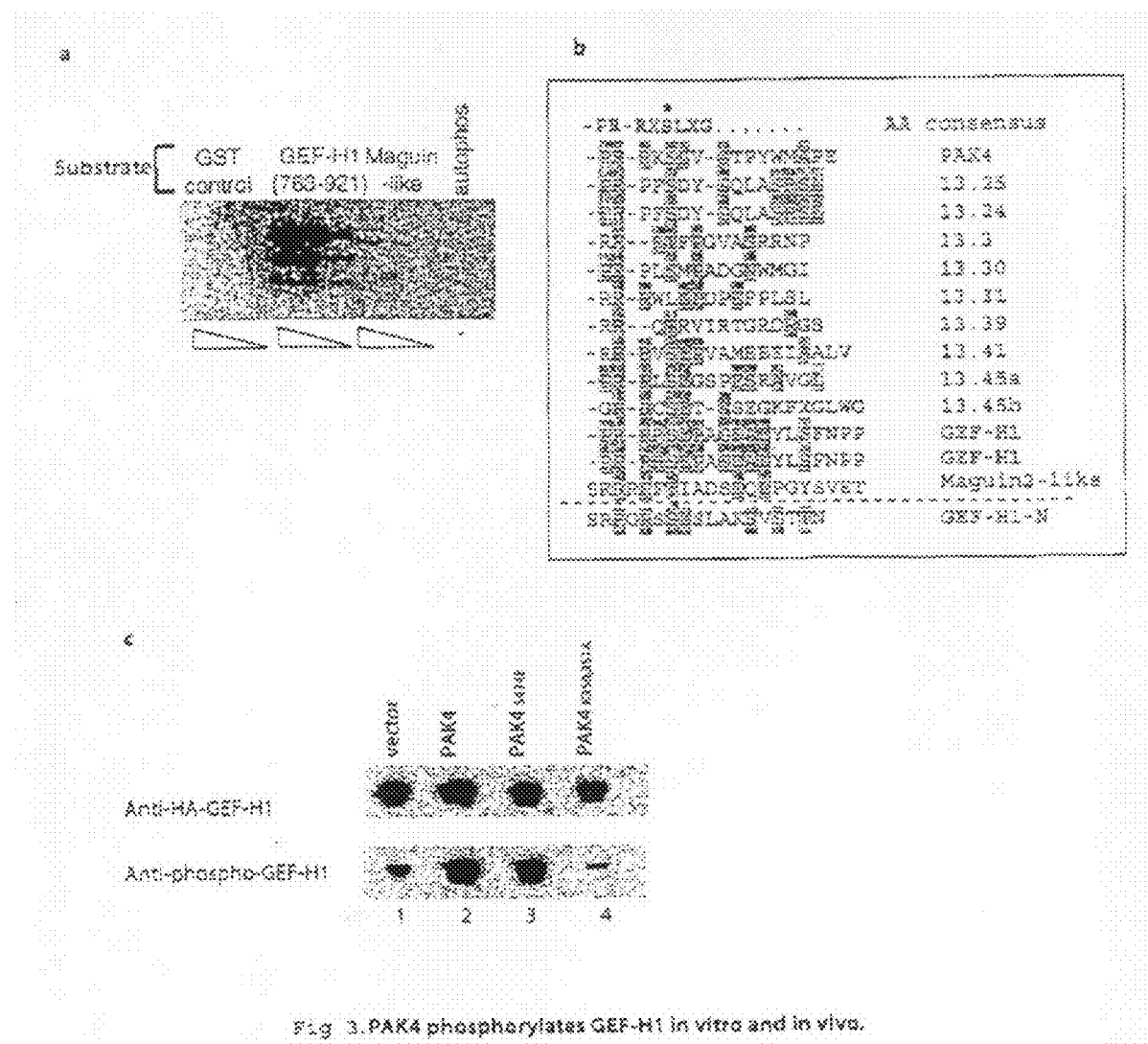
Fig. 3. PAK4 phosphorylates GEF-H1 in vitro and in vivo.

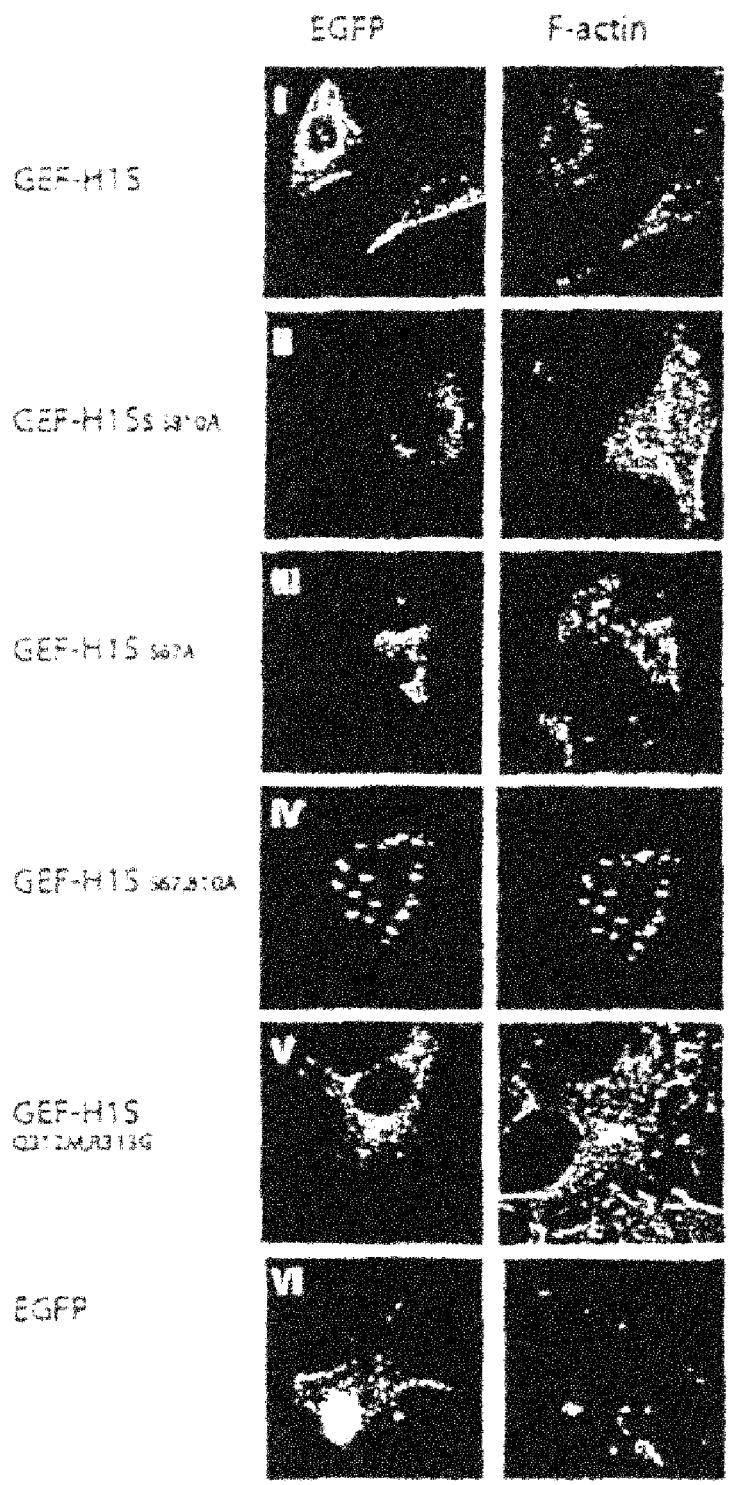
Fig 4. Morphological effects of GEF-H1 alleles.

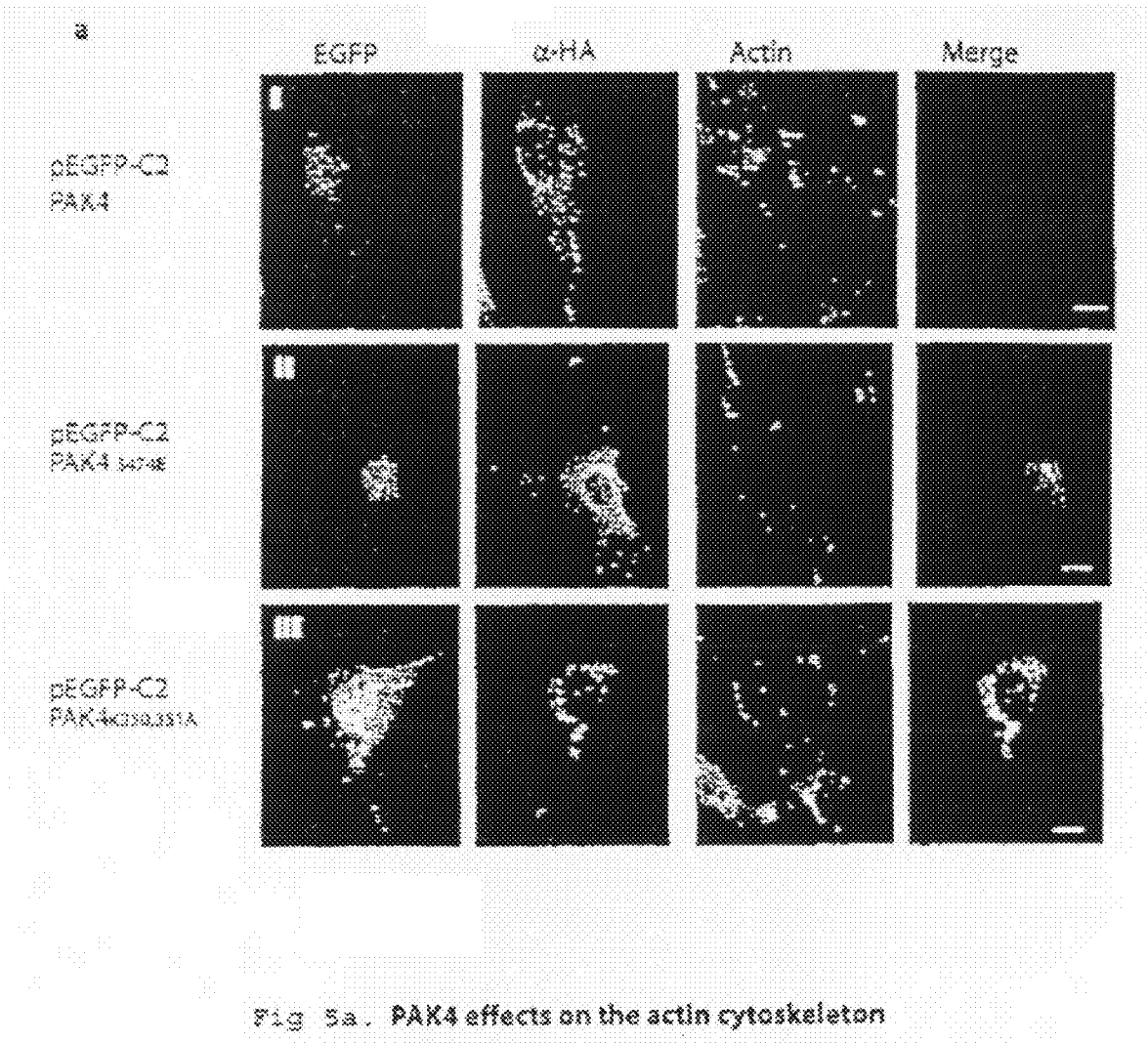
Fig 5a. PAK4 effects on the actin cytoskeleton

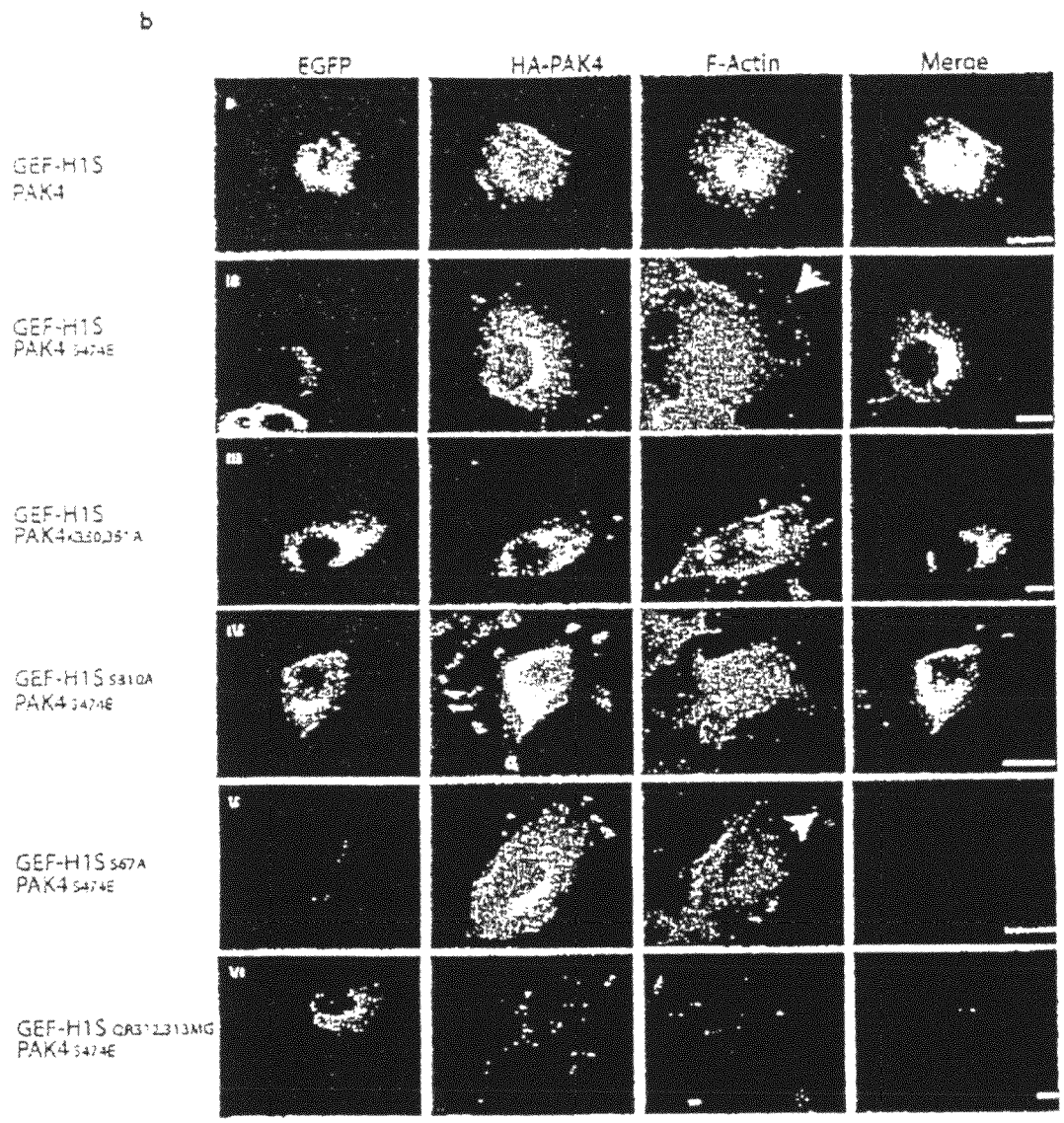
Fig 5b. PAK4 regulates lammellipodia formation through phosphorylation of S810.

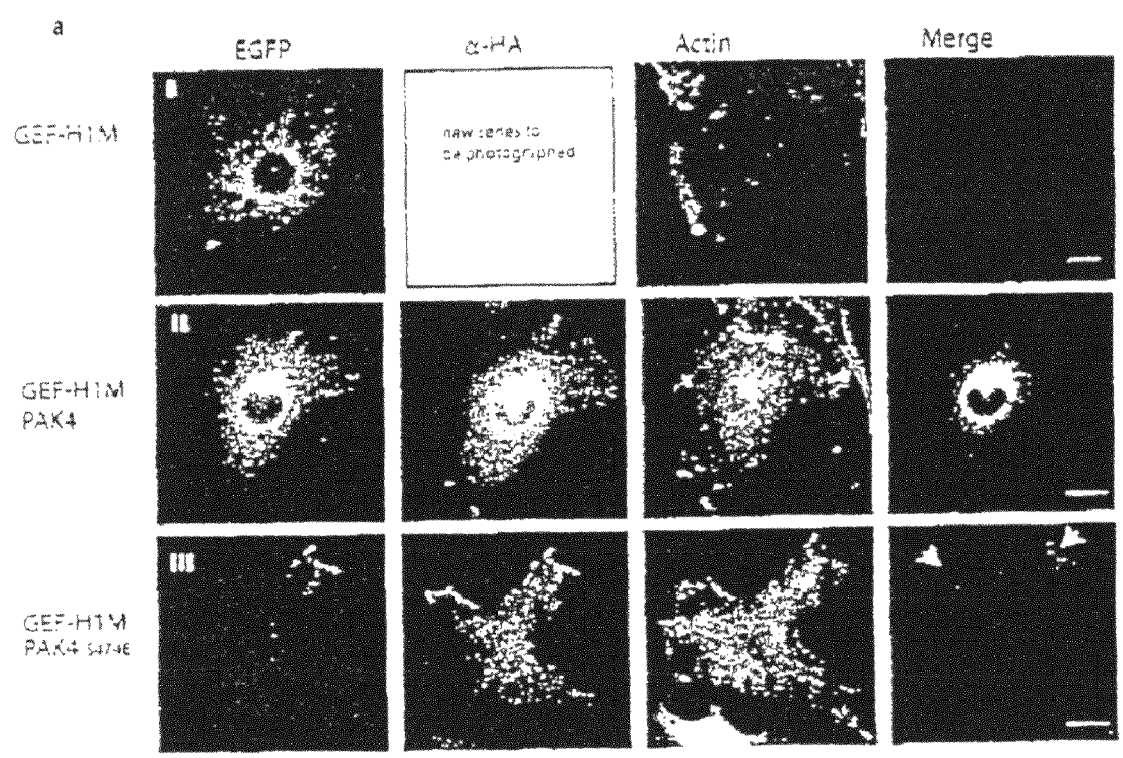
Fig 6a. PAK4 signalling through GEF-H1M to the actin cytoskeleton.

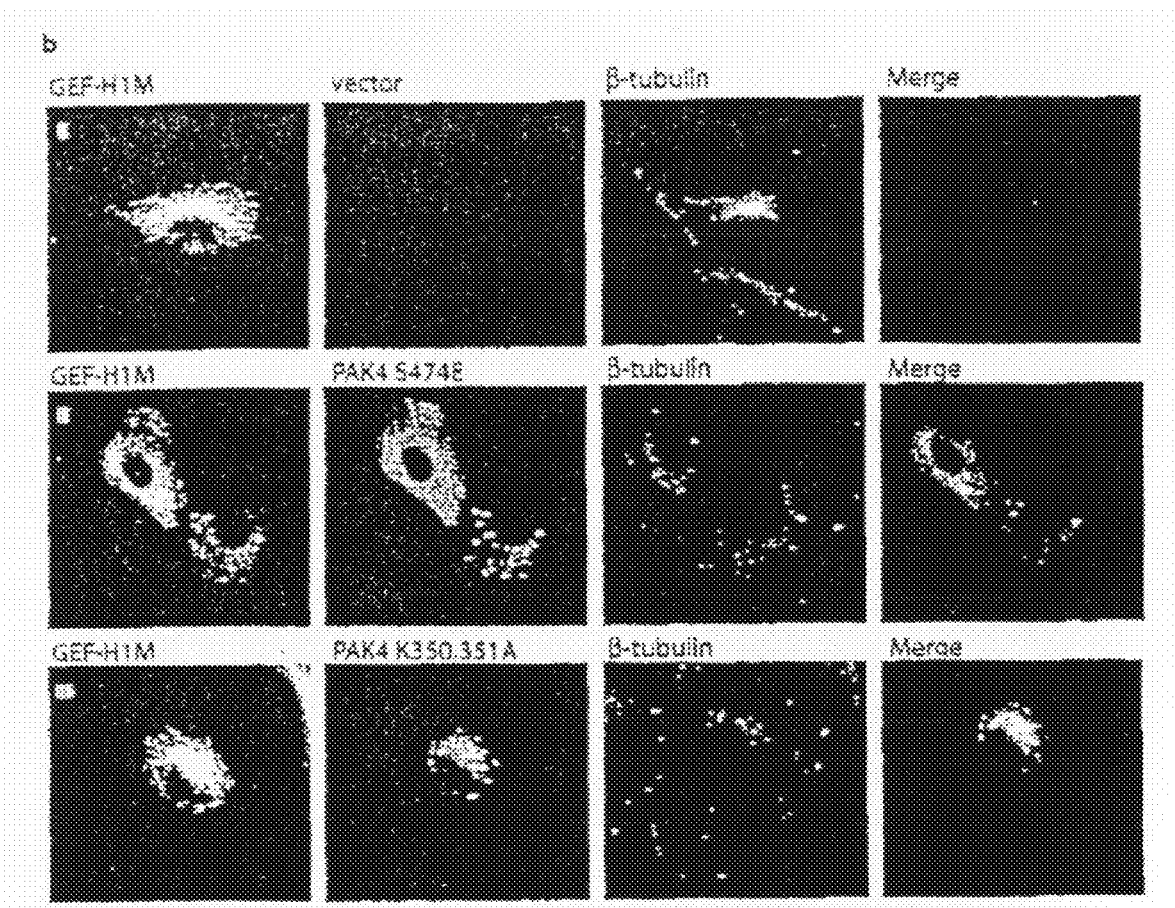
Fig 6b. PAK4 activity destabilizes GEF-H1M association with MTs.

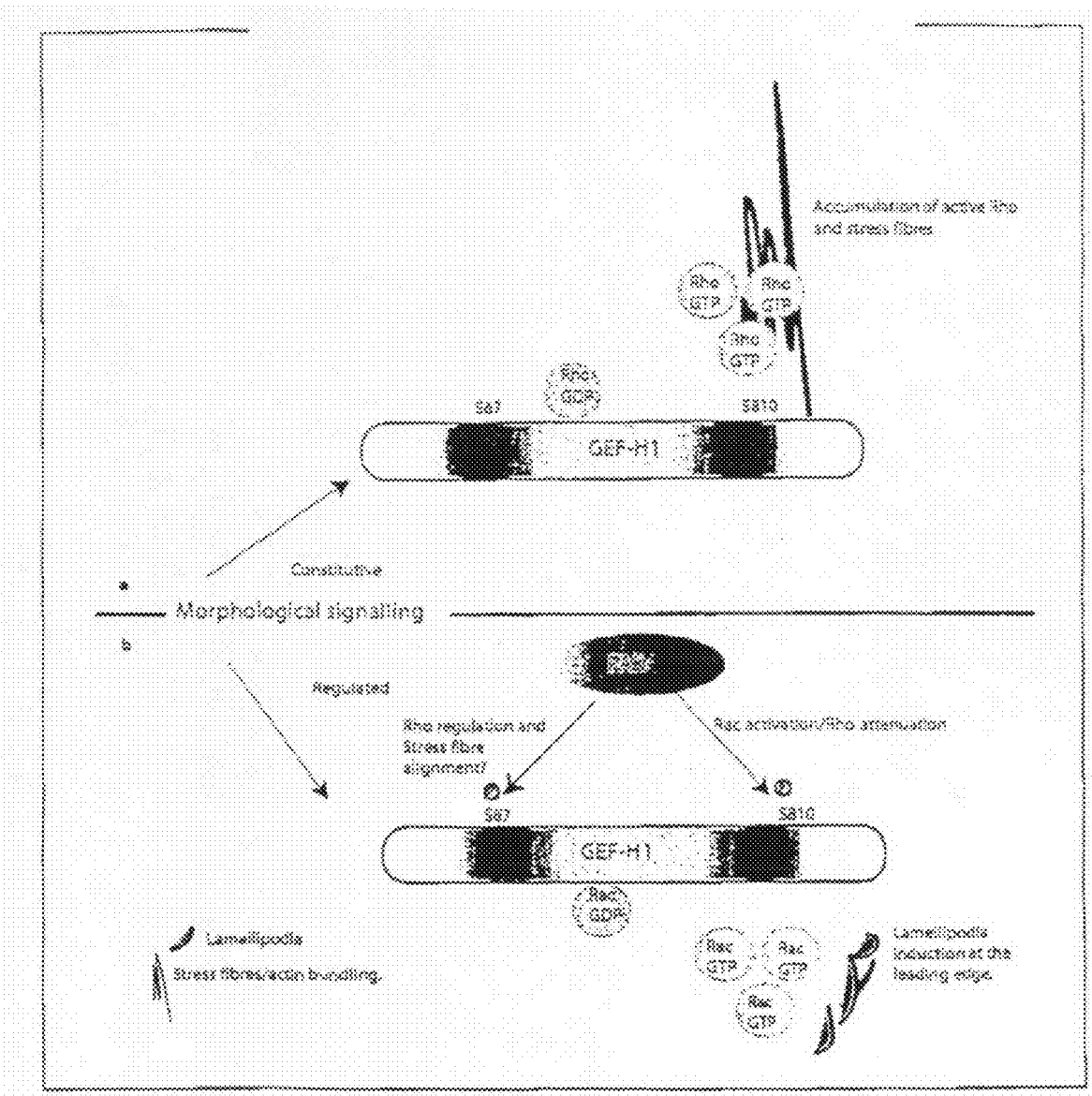
Fig 7. Model for reciprocal regulation of Rac and Rho in vivo.

FIGURE 8    Phosphorylation scores GEF-H1 proteins and peptides.

a.

| | PEPTIDE | | PHOSPHORYLATION |
|---|---|---|---|
| 681 | RRKSLVGTPYWMAPE | PAK4 act loop | +++++ |
| 1008 | RRRSLPAGDALYLSFNPP | GEFH1(807-824) | +++++ |
| 1009 | RRRSLPAGDALYLSFNPP | GEFH1(807-824) | − |
| 1010 | RRRSLPAGDALYLSFNPP | GEFH1(807-824) | +++++ |
| 1412 | RQSLLGSRRGRSSLSLAK | GEFH1(55-72) | − |
| 1413 | RQSLLGSRRGRSSLSLAK | GEFH1(55-72) | − |
| 1414 | RQSLLGSRRGRSSLSLAK | GEFH1(55-72) | ++++ | b.

| POLYPEPTIDE | PHOSPHORYLATION |
|---|---|
| 1-386 | ++++ |
| 386-921 | ++ |
| 763-921 | ++++ |
| 51-921s810A | ++++ |
| 386-921s810A | − |
| 807-824 | ++++ |
| 55-72 | ++ |

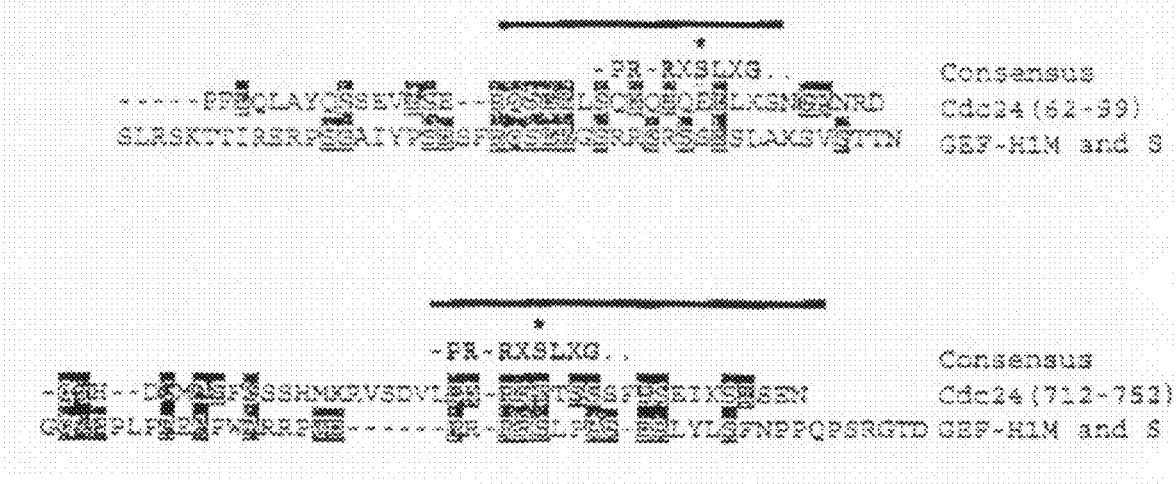
FIGURE 9. GEF-H1 regulatory regions are conserved with Cdc24

SEQUENCE LISTING

<160> NUMBER OF SEQ ID NOS: 52

<210> SEQ ID NO 1
<211> LENGTH: 2763
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgcctgtaa caagagcatc acagccaagg aagccctcat ctgcccaaca acagaaagcg      60
gccctgctga agaacaacac cgccttgcag tccgtttctc ttcgaagtaa gacaaccatc     120
cgggagcggc aagctcggc catctacccc tccgacagct ccggcagtc cctcctgggc      180 tcccgccgtg gccgctcctc cttgtcttta gccaagagtg tttctaccac caacattgct     240
ggacatttca atgatgagtc tcccctgggg ctgcgccgga tcctctcaca gtccacagac     300
tccctcaaca tgcggaaccg aaccctatcc gtggaatccc tcattgacga agcagaggta     360
atctacagtg agctgatgag tgactttgag atggatgaga aggactttgc agctgactct     420
tggagtcttg ctgtggacag cagcttcctg cagcagcata aaaaggaggt gatgaagcag     480
caagatgtca tctatgagct aatccagaca gagctgcacc atgtgaggac actgaagatc     540
atgacccgcc tcttccgcac ggggatgctg gaagagctac acttggagcc aggagtggtc     600
cagggcctgt tccctgcgt ggacgagctc agtgacatcc atacacgctt cctcagccag     660
ctattagaac gccgacgcca ggccctgtgc cctggcagca cccggaactt tgtcatccat     720
cgcttgggtg atctgctcat cagccagttc tcaggtccta gtgcggagca gatgtgtaag     780
acctactcgg agttctgcag ccgccacagc aaggccttaa agctctataa ggagctgtac     840
gcccgagaca aacgcttcca gcaattcatc cggaaagtga cccgccccgc cgtgctcaag     900
cggcacgggg tacaggagtg catcctgctg gtgactcagc gcatcaccaa gtacccgtta     960
ctcatcagcc gcatcctgca gcattccac gggatcgagg aggagcgcca ggacctgacc    1020
acagcactgg ggctagtgaa ggagctgctg tccaatgtgg acgagggtat ttatcagctg    1080
```

```
gagaaagggg cccgtctgca ggagatctac aaccgcatgg accctcgggc ccaaacccca   1140
gtgcctggca agggccccttt tggccgagag aacttctga ggcgcaaact catccacgat    1200
ggctgcctgc tctggaagac agcgacgggg cgcttcaaag atgtgttagt gctgctgatg   1260
acagatgtac tggtgtttct ccaggaaaag gaccagaagt acatctttcc taccctggac   1320
aagccttcag tggtatcgct gcagaatcta atcgtacgag acattgccaa ccaggagaaa   1380
gggatgtttc tgatcagcgc agccccacct gagatgtacg aggtgcacac agcatcccgg   1440
gatgaccgga gcacctggat ccgggtcatt cagcagagcg tgcgcacatg cccatccagg   1500
gaggacttcc ccctgattga gacagaggat gaggcttacc tgcggcgaat taagatggag   1560
ttgcagcaga aggaccgggc actggtggag ctgctgcgag agaaggtcgg gctgttttgct  1620
gagatgaccc catttccagg cgaagaggat ggtggcagtg ggatggccct gcccacctg    1680
cccaggggcc ttttccgctc tgagtcccctt gagtcccctc gtggcgagcg gctgctgcag  1740
gatgccatcc gtgaggtgga gggtctgaaa gacctgctgg tggggccagg agtggaactg   1800
ctcttgacac cccgagagcc agccctgccc ttggaaccag acagcggtgg taacacgagt   1860
cctggggtca ctgccaatgg tgaggccaga accttcaatg gctccattga actctgcaga   1920
gctgactcag actctagcca gagggatcga aatggaaatc agctgagatc accgcaagag   1980
gaggcgttac agcgattggt caatctctat ggacttctac atggcctaca ggcagctgtg   2040
gcccagcagg acactctgat ggaagcccgg ttccctgagg gccctgagcg gcgggagaag   2100
ctgtgccgag ccaactctcg ggatggggag gctggcaggg ctggggctgc ccctgtggcc   2160
cctgaaaagc aggccacgga actggcatta ctgcagcggc aacatgcgct gctgcaggag   2220
gagctacggc gctgccggcg gctaggtgaa gaacgggcaa ccgaagctgg cagcctggag   2280
gcccggctcc gggagagtga gcaggcccgg gcactgctgg agcgtgaggc cgaagaggct   2340
cgaaggcagc tggccgccct gggccagacc gagccactcc cagctgaggc ccctggggcc   2400
cgcagacctg tggatcctcg gcggcgcagc ctccccgcag gcgatgccct gtacttgagt   2460
ttcaaccccc cacagcccag ccgaggcact gaccgcctgg atctacctgt cactactcgc   2520
tctgtccatc gaaactttga ggaccgagag aggcaggaac tggggagccc cgaagagcgg   2580
ctgcaagaca gcagtgaccc tgacactggc agcgaggagg aaggtagcag ccgtctgtct   2640
ccgccccaca gtccacgagg tgagaccctg gcggagacat ggaccagaga ctttaccaga   2700
atgcaggaca tcccggagga gacggagagc cgcgacgggg aggctgtagc ctccgagagc   2760
taa                                                                 2763
```

<210> SEQ ID NO 2
<211> LENGTH: 920
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Pro Val Thr Arg Ala Ser Gln Pro Arg Lys Pro Ser Ser Ala Gln
 1               5                  10                  15

Gln Gln Lys Ala Ala Leu Leu Lys Asn Asn Thr Ala Leu Gln Ser Val
                20                  25                  30

Ser Leu Arg Ser Lys Thr Thr Ile Arg Glu Arg Pro Ser Ser Ala Ile
            35                  40                  45

```
Tyr Pro Ser Asp Ser Phe Arg Gln Ser Leu Leu Gly Ser Arg Arg Gly
     50                  55                  60

Arg Ser Ser Leu Ser Leu Ala Lys Ser Val Ser Thr Thr Asn Ile Ala
 65                  70                  75                  80

Gly His Phe Asn Asp Glu Ser Pro Leu Gly Leu Arg Arg Ile Leu Ser
                 85                  90                  95

Gln Ser Thr Asp Ser Leu Asn Met Arg Asn Arg Thr Leu Ser Val Glu
            100                 105                 110

Ser Leu Ile Asp Glu Ala Glu Val Ile Tyr Ser Glu Leu Met Ser Asp
            115                 120                 125

Phe Glu Met Asp Glu Lys Asp Phe Ala Ala Asp Ser Trp Ser Leu Ala
130                 135                 140

Val Asp Ser Ser Phe Leu Gln Gln His Lys Lys Glu Val Met Lys Gln
145                 150                 155                 160

Gln Asp Val Ile Tyr Glu Leu Ile Gln Thr Glu Leu His His Val Arg
                165                 170                 175

Thr Leu Lys Ile Met Thr Arg Leu Phe Arg Thr Gly Met Leu Glu Glu
                180                 185                 190

Leu His Leu Glu Pro Gly Val Val Gln Gly Leu Phe Pro Cys Val Asp
            195                 200                 205

Glu Leu Ser Asp Ile His Thr Arg Phe Leu Ser Gln Leu Leu Glu Arg
210                 215                 220

Arg Arg Gln Ala Leu Cys Pro Gly Ser Thr Arg Asn Phe Val Ile His
225                 230                 235                 240

Arg Leu Gly Asp Leu Leu Ile Ser Gln Phe Ser Gly Pro Ser Ala Glu
                245                 250                 255

Gln Met Cys Lys Thr Tyr Ser Glu Phe Cys Ser Arg His Ser Lys Ala
            260                 265                 270

Leu Lys Leu Tyr Lys Glu Leu Tyr Ala Arg Asp Lys Arg Phe Gln Gln
            275                 280                 285

Phe Ile Arg Lys Val Thr Arg Pro Ala Val Leu Lys Arg His Gly Val
290                 295                 300

Gln Glu Cys Ile Leu Leu Val Thr Gln Arg Ile Thr Lys Tyr Pro Leu
305                 310                 315                 320

Leu Ile Ser Arg Ile Leu Gln His Ser His Gly Ile Glu Glu Glu Arg
                325                 330                 335

Gln Asp Leu Thr Thr Ala Leu Gly Leu Val Lys Glu Leu Leu Ser Asn
            340                 345                 350

Val Asp Glu Gly Ile Tyr Gln Leu Glu Lys Gly Ala Arg Leu Gln Glu
            355                 360                 365

Ile Tyr Asn Arg Met Asp Pro Arg Ala Gln Thr Pro Val Pro Gly Lys
370                 375                 380

Gly Pro Phe Gly Arg Glu Glu Leu Leu Arg Arg Lys Leu Ile His Asp
385                 390                 395                 400

Gly Cys Leu Leu Trp Lys Thr Ala Thr Gly Arg Phe Lys Asp Val Leu
                405                 410                 415

Val Leu Leu Met Thr Asp Val Leu Val Phe Leu Gln Glu Lys Asp Gln
            420                 425                 430

Lys Tyr Ile Phe Pro Thr Leu Asp Lys Pro Ser Val Val Ser Leu Gln
            435                 440                 445

Asn Leu Ile Val Arg Asp Ile Ala Asn Gln Glu Lys Gly Met Phe Leu
450                 455                 460

Ile Ser Ala Ala Pro Pro Glu Met Tyr Glu Val His Thr Ala Ser Arg
```

```
                465                 470                 475                 480

Asp Asp Arg Ser Thr Trp Ile Arg Val Ile Gln Gln Ser Val Arg Thr
                485                 490                 495

Cys Pro Ser Arg Glu Asp Phe Pro Leu Ile Glu Thr Glu Asp Glu Ala
                500                 505                 510

Tyr Leu Arg Arg Ile Lys Met Glu Leu Gln Gln Lys Asp Arg Ala Leu
                515                 520                 525

Val Glu Leu Leu Arg Glu Lys Val Gly Leu Phe Ala Glu Met Thr His
                530                 535                 540

Phe Gln Ala Glu Glu Asp Gly Gly Ser Gly Met Ala Leu Pro Thr Leu
545                 550                 555                 560

Pro Arg Gly Leu Phe Arg Ser Glu Ser Leu Glu Ser Pro Arg Gly Glu
                565                 570                 575

Arg Leu Leu Gln Asp Ala Ile Arg Glu Val Glu Gly Leu Lys Asp Leu
                580                 585                 590

Leu Val Gly Pro Gly Val Glu Leu Leu Thr Pro Arg Glu Pro Ala
                595                 600                 605

Leu Pro Leu Glu Pro Asp Ser Gly Gly Asn Thr Ser Pro Gly Val Thr
610                 615                 620

Ala Asn Gly Glu Ala Arg Thr Phe Asn Gly Ser Ile Glu Leu Cys Arg
625                 630                 635                 640

Ala Asp Ser Asp Ser Ser Gln Arg Asp Arg Asn Gly Asn Gln Leu Arg
                645                 650                 655

Ser Pro Gln Glu Glu Ala Leu Gln Arg Leu Val Asn Leu Tyr Gly Leu
                660                 665                 670

Leu His Gly Leu Gln Ala Val Ala Gln Gln Asp Thr Leu Met Glu
                675                 680                 685

Ala Arg Phe Pro Glu Gly Pro Glu Arg Glu Lys Leu Cys Arg Ala
                690                 695                 700

Asn Ser Arg Asp Gly Glu Ala Gly Arg Ala Gly Ala Ala Pro Val Ala
705                 710                 715                 720

Pro Glu Lys Gln Ala Thr Glu Leu Ala Leu Leu Gln Arg Gln His Ala
                725                 730                 735

Leu Leu Gln Glu Glu Leu Arg Arg Cys Arg Arg Leu Gly Glu Glu Arg
                740                 745                 750

Ala Thr Glu Ala Gly Ser Leu Glu Ala Arg Leu Arg Glu Ser Glu Gln
                755                 760                 765

Ala Arg Ala Leu Leu Glu Arg Glu Ala Glu Ala Arg Arg Gln Leu
                770                 775                 780

Ala Ala Leu Gly Gln Thr Glu Pro Leu Pro Ala Glu Ala Pro Trp Ala
785                 790                 795                 800

Arg Arg Pro Val Asp Pro Arg Arg Ser Leu Pro Ala Gly Asp Ala
                805                 810                 815

Leu Tyr Leu Ser Phe Asn Pro Pro Gln Pro Ser Arg Gly Thr Asp Arg
                820                 825                 830

Leu Asp Leu Pro Val Thr Thr Arg Ser Val His Arg Asn Phe Glu Asp
                835                 840                 845

Arg Glu Arg Gln Glu Leu Gly Ser Pro Glu Glu Arg Leu Gln Asp Ser
                850                 855                 860

Ser Asp Pro Asp Thr Gly Ser Glu Glu Gly Ser Ser Arg Leu Ser
865                 870                 875                 880

Pro Pro His Ser Pro Arg Gly Glu Thr Leu Ala Glu Thr Trp Thr Arg
                885                 890                 895
```

-continued

```
Asp Phe Thr Arg Met Gln Asp Ile Pro Glu Glu Thr Glu Ser Arg Asp
            900                 905                 910

Gly Glu Ala Val Ala Ser Glu Ser
        915                 920

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Ser Leu Pro Ala Gly Asp Ala Leu Tyr Leu Ser Phe Asn
  1               5                  10                  15

Pro Pro

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gln Ser Leu Leu Gly Ser Arg Arg Gly Arg Ser Ser Leu Ser Leu
  1               5                  10                  15

Ala Lys

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Glu Thr Leu Ala Glu Thr Trp Thr
  1               5                  10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: basic amino acid
<220> FEATURE:
<221> NAME/KEY: MOD_RES
<222> LOCATION: (4)
<223> OTHER INFORMATION: hydrophobic amino acid
<220> FEATURE:
<221> NAME/KEY: MOD_RES
<222> LOCATION: (5)
<223> OTHER INFORMATION: any amino acid

<400> SEQUENCE: 6

Arg Xaa Ser Xaa Xaa Gly
  1               5
```

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Pro Arg Arg Arg Ser Leu Pro Ala Gly Asp Ala Leu Tyr Leu Ser
  1               5                  10                  15

Phe Asn Pro Pro
            20

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Arg Gln Ser Leu Leu Gly Ser Arg Arg Gly Arg Ser Ser Leu Ser
  1               5                  10                  15

Leu Ala Lys

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Arg Gln Ser Leu Leu Gly Ser Arg Arg Gly Arg Ser Ser Leu Ser
  1               5                  10                  15

Leu Ala Lys

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgtagatcct cggcggcgcg ctctccccgc a                                    31

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggtgatgccc atggtctcca gcaggat                                         27

<210> SEQ ID NO 12
<211> LENGTH: 28
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 12
atcctgctgg tgaccatggg catcacca                                          28

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gccgtggccg ctccgccttg tcttta                                            26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taaagacaag gcggagcggc cacggc                                            26

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Arg Ile Thr Lys Tyr
  1               5

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcagaattct gtaacaagag catcaca                                           27

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgctcgagt tagctctcgg aggctacagc ct                                     32

<210> SEQ ID NO 18
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Arg Arg Lys Ser Leu Val Gly Thr Pro Tyr Trp Met Ala Pro Glu
 1               5                  10                  15

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: phosphorylated Thr

<400> SEQUENCE: 19

Leu Cys Leu Cys Arg Arg Lys Ser Leu Val Gly Thr Pro Tyr Trp Met
 1               5                  10                  15

Ala Pro Glu

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: basic amino acid
<220> FEATURE:
<221> NAME/KEY: MOD_RES
<222> LOCATION: (4)
<223> OTHER INFORMATION: hydrophobic amino acid
<220> FEATURE:
<221> NAME/KEY: MOD_RES
<222> LOCATION: (5)
<223> OTHER INFORMATION: any amino acid

<400> SEQUENCE: 20

Arg Xaa Ser Xaa Xaa Leu
 1               5

<210> SEQ ID NO 21
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Cys Thr Pro Ala Ala Pro Ala Val Pro Ala Val Pro Gly Pro Pro Gly
 1               5                  10                  15

Pro Arg Ser Pro Gln Arg Glu Pro Gln Arg Val Ser His Glu Gln Phe
                20                  25                  30

Arg Ala Ala Leu Gln Leu Val Val Asp Pro Gly Asp Pro Arg Ser Tyr
            35                  40                  45

Leu Asp Asn Phe
    50
```

```
<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Arg Val Ser His Glu Gln Phe Arg Ala Ala Leu Gln Leu Val Val Asp
 1               5                  10                  15

Pro Gly Asp Pro Arg Ser Tyr Leu Asp
            20                  25

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Ser Gly Asp Arg Arg Arg Ala Gly Pro Glu Lys Arg Pro Lys Ser
 1               5                  10                  15

Ser

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: any amino acid
<220> FEATURE:
<221> NAME/KEY: MOD_RES
<222> LOCATION: (6)..(7)
<223> OTHER INFORMATION: any amino acid and this range may encompass one
      or two residues

<400> SEQUENCE: 24

Arg Arg Xaa Ser Leu Xaa Xaa Gly
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: any basic amino acid
<220> FEATURE:
<221> NAME/KEY: MOD_RES
<222> LOCATION: (4)
<223> OTHER INFORMATION: any hydrophobic amino acid
<220> FEATURE:
<221> NAME/KEY: MOD_RES
<222> LOCATION: (5)
<223> OTHER INFORMATION: any amino acid
<220> FEATURE:
<221> NAME/KEY: MOD_RES
<222> LOCATION: (6)
```

```
<223> OTHER INFORMATION: Gly or Leu

<400> SEQUENCE: 25

Arg Xaa Ser Xaa Xaa Xaa
 1               5

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcggaattca tgtctcggat cgaatccctc a                                   31

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtcactgagc tcgtccacgc agggga                                         26

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: phosphorylated Ser

<400> SEQUENCE: 28

Arg Arg Arg Ser Leu Pro Ala Gly Asp Ala Leu Tyr Leu Ser Phe Asn
 1               5                  10                  15

Pro Pro

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: phosphorylated Ser

<400> SEQUENCE: 29

Arg Arg Arg Ser Leu Pro Ala Gly Asp Ala Leu Tyr Leu Ser Phe Asn
 1               5                  10                  15

Pro Pro

<210> SEQ ID NO 30
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: phosphorylated Tyr

<400> SEQUENCE: 30

Arg Arg Arg Ser Leu Pro Ala Gly Asp Ala Leu Tyr Leu Ser Phe Asn
  1               5                  10                  15

Pro Pro

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Ala Thr Thr Ala Arg Gly Gly Pro Gly Lys Ala Gly Ser Arg Gly
  1               5                  10                  15

Arg Phe Ala Gly His Ser Glu Ala
            20

<210> SEQ ID NO 32
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Thr Pro Ala Ala Pro Ala Val Pro Gly Pro Pro Gly Pro Arg Ser
  1               5                  10                  15

Pro Gln Arg Glu Pro Gln Arg Val Ser His Glu Gln Phe Arg Ala Ala
                20                  25                  30

Leu Gln Leu Val Val Asp Pro Gly Asp Pro Arg Ser Tyr Leu Asp Asn
            35                  40                  45

Phe

<210> SEQ ID NO 33
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Tyr Leu Ser Ser Leu Ser Leu Ser Ser Thr Tyr Pro Pro Pro
  1               5                  10                  15

Ser Trp Gly Ser Ser Ser Asp Gln Gln Pro Ser Arg Val Ser His Glu
                20                  25                  30

Gln Phe Arg Ala Ala Leu Gln Leu Val Val Ser Pro Gly Asp Pro Arg
            35                  40                  45

Glu Tyr Leu Ala Asn Phe Ile Lys
        50                  55

<210> SEQ ID NO 34
<211> LENGTH: 54
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Ser Thr Ser Asn Leu Tyr Leu Pro Gln Asp Pro Thr Val Ala Lys
 1               5                  10                  15

Gly Ala Leu Ala Gly Glu Asp Thr Gly Val Val Thr His Glu Gln Phe
                20                  25                  30

Lys Ala Ala Leu Arg Met Val Val Asp Gln Gly Asp Pro Arg Leu Leu
            35                  40                  45

Leu Asp Ser Tyr Val Lys
        50

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (7)
<223> OTHER INFORMATION: Variable amino acid

<400> SEQUENCE: 35

Pro Arg Arg Xaa Ser Leu Xaa Gly
 1               5

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Arg Arg Lys Ser Leu Val Gly Thr Pro Tyr Trp Met Ala Pro Glu
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Arg Pro Phe Ser Asp Tyr Gly Gln Leu Ala Ser Arg Ser Leu
 1               5                  10                  15

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Arg Arg Arg Thr Phe Pro Gly Val Ala Ser Arg Arg Asn Pro
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Arg Pro Leu Ser Met Pro Ala Asp Gly Asn Trp Met Gly Ile
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Arg Arg Trp Leu Leu Pro Asp Pro Glu Phe Pro Leu Ser Leu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Arg Gln Thr Arg Val Ile Arg Thr Gly Arg Asp Arg Gly Ser
1               5                   10                  15

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Arg Val Ser Leu Pro Val Ala Met Glu Glu Ile Ala Ala
1               5                   10                  15

Leu Val

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Arg Arg Leu Ser Leu Gly Ser Pro Glu Ser Arg Ala Val Gly Leu
1               5                   10                  15

<210> SEQ ID NO 44
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Variable or undetermined amino acid

<400> SEQUENCE: 44

Gly Arg Arg Cys Ser Leu Thr Gly Ser Glu Gly Lys Phe Xaa Gly Leu
 1               5                  10                  15

Trp Gly

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Arg Arg Arg Ser Leu Pro Ala Gly Asp Ala Leu Tyr Leu Ser Phe
 1               5                  10                  15

Asn Pro Pro

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Arg Arg Arg Arg Phe Thr Ile Ala Asp Ser Asp Gln Leu Pro Gly
 1               5                  10                  15

Tyr Ser Val Glu Thr
            20

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Arg Arg Gly Arg Ser Ser Leu Ser Leu Ala Lys Ser Val Ser Thr
 1               5                  10                  15

Thr Asn

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Phe Leu Gln Leu Ala Tyr Gln Ser Ser Glu Val Leu Ser Glu Arg
```

```
                    1               5                  10                 15
Gln Ser Leu Leu Leu Ser Gln Lys Gln His Gln Glu Leu Leu Lys Ser
                        20                  25                 30

Asn Gly Ala Asn Arg Asp
            35

<210> SEQ ID NO 49
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu Arg Ser Lys Thr Thr Ile Arg Glu Arg Pro Ser Ser Ala Ile
  1               5                  10                 15

Tyr Pro Ser Asp Ser Phe Arg Gln Ser Leu Leu Gly Ser Arg Arg Gly
                    20                  25                  30

Arg Ser Ser Leu Ser Leu Ala Lys Ser Val Ser Thr Thr Asn
            35                  40                  45

<210> SEQ ID NO 50
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Thr His Asp Ser Met Ala Ser Phe Ser Ser Ser His Met Lys Arg
  1               5                  10                 15

Val Ser Asp Val Leu Pro Lys Arg Arg Thr Thr Ser Ser Ser Phe Glu
                    20                  25                  30

Ser Glu Ile Lys Ser Ile Ser Glu Asn
            35                  40

<210> SEQ ID NO 51
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gln Thr Glu Pro Leu Pro Ala Glu Ala Pro Trp Ala Arg Arg Pro
  1               5                  10                 15

Val Asp Pro Arg Arg Arg Ser Leu Pro Ala Gly Asp Ala Leu Tyr Leu
                    20                  25                  30

Ser Phe Asn Pro Pro Gln Pro Ser Arg Gly Thr Asp
            35                  40

<210> SEQ ID NO 52
<211> LENGTH: 19
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 52

Cys Arg Arg Arg Ser Leu Pro Ala Gly Asp Ala Leu Tyr Leu Ser Phe
 1               5                  10                  15

Asn Pro Pro
```

GEF-H1B: BIOMARKERS, COMPLEXES, ASSAYS AND THERAPEUTIC USES THEREOF

CROSS-REFERENCE TO RELATED PATENT APPLICATIONS

This application is a Divisional application of U.S. patent application Ser. No. 10/611,671, filed Jul. 2, 2003, now U.S. Pat. No. 7,439,329, which in turn claims priority from U.S. Provisional Application Nos. 60/460,053, filed Apr. 4, 2003, and 60/393,600, filed Jul. 5, 2002, which are all incorporated by reference in their entirety.

FIELD OF THE INVENTION

The instant invention relates to diagnosing abnormal cell proliferation in biological samples and screening for drugs which inhibit, reduce or abolish cell growth, especially tumorigenic cell growth, by detecting a phosphovariant isoform of a novel guanine nucleotide exchange factor biomarker.

BACKGROUND OF THE INVENTION

Guanine nucleotide exchange factors ("GEFs") stimulate the dissociation of the GTP hydrolytic product, GDP, from small GTP-binding proteins, to promote the binding of a new GTP molecule. In doing so, this GEF-facilitated exchange of GDP for GTP is associated with structural changes in the GTP-binding protein which influence the degree to which the GTP-binding protein can interact with other molecules. When GTP is bound, for instance, Ras proteins can interact with effectors and other molecules to affect cell proliferation, differentiation and apoptosis.

The possible importance of GEFs in the spatial localization of changes in the actin cytoskeleton is beginning to be understood. See, Shamah et al., *Cell,* 20:105(2):233-44, 2001. From an evolutionary perspective this spatial control is satisfied in that the distant relative *S. cerevisiae* Cdc24, a GEF for Cdc42, plays a key role in targeting cytoskeletal changes to different spatial domains of the cell in response to different signals O'Shea et al., *Nature Cell Biol.,* 2(3):E39-41, 2000.

Thus, existing techniques and current knowledge have not used nor addressed the interactions of GEF-H1 with other proteins as a means by which cell proliferation can be controlled or the detection and treatment of cancerous, tumorigenic cells and tissues be developed.

SUMMARY OF THE INVENTION

Accordingly, the present invention envisions an isolated nucleic acid encoding the GEF-H1S polypeptide of SEQ ID NO:2, as well as an isolated nucleic acid comprising the sequence of SEQ ID NO:1. In this context, the invention also contemplates an isolated GEF-H1S polypeptide comprising the sequence of SEQ ID NO:2.

In another embodiment, an isolated nucleic acid encoding the GEF-H1 peptide of SEQ ID NO:3 is provided. The invention also envisages a peptide consisting essentially of the sequence of SEQ ID NO. 3. In similar fashion, one other embodiment provides an isolated nucleic acid encoding the GEF-H1 peptide of SEQ ID NO:4. In another embodiment, a peptide consisting essentially of the sequence of SEQ ID NO. 4 is also provided. In a preferred embodiment, a GEF-H1 polypeptide is provided that lacks the amino acid region between residues 162 and 354 of SEQ ID NO. 2. In a preferred embodiment, the GEF-H1 is GEF-H1S. The present invention envisions phosphorylated forms of any one of these GEF-H1 peptides, polypeptides and proteins. Thus, in one embodiment, peptides comprising the sequences described in SEQ ID NOs. 2, 3 or 4, that contain at least one phosphorylated residue, are provided. In a preferred embodiment, the phosphorylated residue is a serine. In a preferred embodiment, the serine is serine-67 and/or serine-810 of SEQ ID NO. 2. In another embodiment, serine-67 is present in a peptide of less than 30 amino acids that comprises the sequence of SEQ ID NO. 4. In another embodiment, the peptide comprising the sequence of SEQ ID NO. 4 is less than 25 amino acids in length. Preferably, this peptide is less than 20 amino acids in length. In a more preferred embodiment, the peptide comprising the sequence of SEQ ID NO. 4 is 18 amino acids long.

In another embodiment, serine-810 is present in a peptide of less than 30 amino acids that comprises the sequence of SEQ ID NO. 3. In another embodiment, the peptide comprising the sequence of SEQ ID NO. 3 is less than 25 amino acids in length. Preferably, this peptide is less than 20 amino acids in length. In a more preferred embodiment, the peptide comprising the sequence of SEQ ID NO. 3 is 18 amino acids long.

The present invention also contemplates antibodies raised to detect any one of these peptides, polypeptides or proteins. Thus, in one embodiment, a GEF-H1-specific antibody is provided that is raised against, and binds to, a peptide comprising the sequence described in SEQ ID NO. 3. In another embodiment, a GEF-H1-specific antibody is provided that is directed against, and binds to, a peptide comprising the sequence described in SEQ ID NO. 4. Antibodies of the present invention may be labeled. Preferably the label is a fluorescent label or a radioactive label.

In another embodiment, the antibody is a part of a diagnostic kit used for performing the inventive methods described herein. Thus, in one embodiment, the kit includes a first container containing the antibody and a second container having a conjugate of a binding partner of the antibody and a label, such as, for example, a radioisotope. In another embodiment, the diagnostic kit may also include notification of an FDA approved use and instructions therefor.

In yet another embodiment, a hybridoma cell line which produces an antibody having specific binding affinity to a GEF-H1 polypeptide or a polypeptide domain is provided.

In yet another embodiment, a GEF-H1-specific antibody is directed against, and binds to, phosphorylated GEF-H1 peptides. Thus, one embodiment realizes a peptide comprising the sequence described in SEQ ID NO. 3 that possesses a phosphorylated serine. Preferably, the phosphorylated serine in that peptide is serine-810 of SEQ ID NO. 2. In another embodiment, the GEF-H1-specific antibody is directed against, and binds to, a peptide comprising the sequence described in SEQ ID NO. 4, wherein serine-67 is phosphorylated. The numbering of these serines in SEQ ID NOs. 3 and 4 as serine-810 and serine-67 respectively indicates the numbering of the full-length protein sequence of GEF-H1, specifically GEF-H1S of SEQ ID NO. 2.

Other peptides envisioned by the present invention include a peptide comprising at least one of SEQ ID NO. 6 or SEQ ID NO. 20. In another embodiment, a peptide consisting essentially of at least one of SEQ ID NO. 6 or SEQ ID NO. 20 is provided. In yet another embodiment, a peptide of less than 30 amino acids comprising the sequence of SEQ ID NO. 6 is provided. In another embodiment, the peptide comprising the sequence of SEQ ID NO. 6 is less than 25 amino acids in length. Preferably, this peptide is less than 20 amino acids in length. In a more preferred embodiment, the peptide comprising the sequence of SEQ ID NO. 6 is 18 amino acids long.

In yet another embodiment, a peptide of less than 30 amino acids comprising the sequence of SEQ ID NO. 20 is provided. In another embodiment, the peptide comprising the sequence of SEQ ID NO. 20 is less than 25 amino acids in length. Preferably, this peptide is less than 20 amino acids in length. In a more preferred embodiment, the peptide comprising the sequence of SEQ ID NO. 20 is 18 amino acids long.

Nucleic acids encoding GEF-H1 proteins of the present invention also are contemplated. Thus, in one embodiment, a polynucleotide comprising the sequence of SEQ ID NO. 1 is provided. In another embodiment, a polynucleotide encoding the polypeptide described in any one of SEQ ID NOs. 2, 3, 4, 6 or 20 is provided. In yet another embodiment a nucleic acid molecule that is less than 90 nucleotides in length and which encodes a peptide comprising the sequence described in SEQ ID NO. 3 or SEQ ID NO. 4, is provided. Preferably, the polynucleotide is less than 75 nucleotides in length, more preferably less than 60 nucleotides in length and most preferably 54 nucleotides in length.

The present invention also contemplates a vector comprising the polynucleotide encoding a GEF-H1S protein comprising the sequence described in SEQ ID NO. 2. In another embodiment, the vector is present in a cell. In another embodiment, the vector comprises a polynucleotide comprising a sequence of SEQ ID NOs. 3 or 4. In another embodiment, the vector is present in a cell.

Another embodiment of the invention is a cell comprising a nucleic acid comprising the nucleotide sequence of SEQ ID NO. 1. In yet another embodiment, a cell is provided that contains a protein comprising the sequence described in SEQ ID NO. 2. In another embodiment, the cell is a bacterial, fungal or mammalian cell.

The present invention provides an isolated GEF-H1/protein complex, wherein a protein binds to GEF-H1 to form the complex. In one embodiment, the protein in the complex is a kinase. Thus, the present invention envisions a GEF-H1-kinase complex. In a further embodiment, the kinase is a serine and/or threonine kinase. In a preferred embodiment the kinase of the GEF-H1-kinase complex is a p-21 activated kinase ("PAK"). In a more preferred embodiment, the PAK is selected from the group consisting of PAK4, PAK5 and PAK6. In an even more preferred embodiment, the PAK of a GEF-H1/PAK complex is PAK4.

The present invention provides methods to identify substances, such as compounds, chemicals, drugs, proteins or nucleic acids, that inhibit, or modulate, the interaction between GEF-H1 proteins and PAK proteins, or which inhibit, or modulate the kinase activity of PAK. In a preferred embodiment, the PAK protein modulated or inhibited by an identified substance is PAK4, PAK5 or PAK6. Most preferably, the PAK is PAK4. In another embodiment, an identified substance modulates or inhibits GEF-H1S binding to PAK proteins, or modulates the expression levels of GEF-H1 genes.

In another aspect of the invention, a method ("method 1") for detecting PAK4 activity in a sample is provided. This method comprises detecting the presence or level of phosphorylated GEF-H1 in the sample, wherein the detection of phosphorylated GEF-H1 indicates that the sample also contains at least one active PAK4. In one embodiment, the GEF-H1 comprises the sequence described in any one of SEQ ID NOs. 2, 3 or 4. In another embodiment, the PAK4 is detected in a sample of cells. In another embodiment, the sample is a preparation of proteins isolated from a cell lystate. In another embodiment, the cells are tumor cells. In a preferred embodiment, tumor cell is in a mammal. In yet another embodiment, the mammal is selected from the group consisting of a human, rat, mouse, dog, rabbit, pig, sheep, cow, horse, cat, primate, goat, or monkey. In a most preferred embodiment, the mammal is a human.

In yet another aspect, a method of identifying a substance that modulates the interaction between PAK4 and GEF-H1 polypeptide is provided by the present invention. This method comprises (a) exposing a GEF-H1 polypeptide to a candidate substance to form a mixture; (b) introducing into the mixture a PAK4 enzyme; and then (c) measuring the amount of GEF-H1 polypeptide phosphorylated before and after exposing the GEF-H1 polypeptide to the candidate substance. In one embodiment, a decrease or increase in the amount of phosphorylated GEF-H1 polypeptide after exposure to the candidate substance indicates that the candidate substance is a substance that modulates the interaction between PAK4 and GEF-H1 polypeptide. In a preferred embodiment, the GEF-H1 polypeptide comprises the sequence of any one of SEQ ID NO. 2, SEQ ID NO. 3 or SEQ ID NO. 4.

A method ("method 2") of identifying a substance that modulates the interaction between PAK4 and GEF-H1 polypeptide is also provided herein. This method comprises (a) exposing PAK4 to a candidate substance to form a mixture; b) introducing into the mixture a GEF-H1 polypeptide; and then (c) measuring the amount of GEF-H1 polypeptide phosphorylated, wherein a decrease or increase in the amount of phosphorylated GEF-H1 polypeptide in comparison to a control in which PAK4 is not exposed to the candidate substance indicates that the candidate substance is a substance that modulates the interaction between PAK4 and GEF-H1 polypeptide.

In a preferred embodiment, the GEF-H1 polypeptide comprises the sequence of any one of SEQ ID NO. 2, SEQ ID NO. 3 or SEQ ID NO. 4.

In another embodiment, the step of determining whether GEF-H1 is phosphorylated in methods 1 or 2 is performed by using a GEF-H1-specific antibody directed against a peptide comprising at least one of phosphorylated serine-810 of SEQ ID NO. 2 or phosphorylated serine-67 of SEQ ID NO. 2.

In a preferred embodiment, the candidate substance causes a decrease in total levels of GEF-H1 phosphorylation.

In another aspect, a method ("method 3") for identifying a substance that modulates the interaction between PAK4 and GEF-H1S is provided by the present invention. This method comprises (i) contacting a candidate substance with a GEF-H1/PAK4 complex and then (ii) determining whether the compound disrupts the complex. In a preferred embodiment, the GEF-H1 is GEF-H1S comprising the sequence of SEQ ID NO. 2.

Yet another method ("method 4") is provided by the present invention and is used to determine whether a candidate substance inhibits PAK4 kinase activity in a mammal. This method comprises (i) measuring, in a mammal, the level of phosphorylation of a GEF-H1 protein comprising the sequence of SEQ ID NO. 2; (ii) exposing the mammal to a candidate substance; and then (iii) measuring in the mammal the level of phosphorylation of the GEF-H1 protein, wherein a decrease in the level of phosphorylation of the GEF-H1 protein in step (iii) relative to the level measured in step (i) indicates that the candidate substance is an inhibitor of PAK4 kinase. In another embodiment, the detection of phosphorylated GEF-H1 proteins after administration of the candidate substance indicates that the drug may not inhibit PAK4 kinase activity. In another embodiment, the ratio of the level of GEF-H1 phosphorylation before application of the candidate substance to the level of GEF-H1 phosphorylation after application of the candidate substance, is also determined by comparing the ratio to a "background" level of GEF-H1 phosphorylation cells and/or cell lysates that have not been treated with the candidate substance.

In a preferred embodiment, the mammal is a human, rat, mouse, dog, rabbit, pig, sheep, cow, horse, cat, primate, goat, or monkey. In a most preferred embodiment, the mammal is a human.

The candidate substance identified by any one of the methods described herein may be used, for example, to treat cancer, reduce cell proliferation or reduce anchorage-independent cell growth. Thus, a method ("method 5") for treating cancer in a mammal is envisioned by the present invention, comprising administering to the mammal a substance identified by one of the present methods as modulating or inhibiting GEF-H1 activity or modulating or inhibiting PAK4 and GEF-H1 interaction.

In yet one other aspect, the present invention provides a method ("method 6") for determining the presence of activated PAK4 in a cell sample. Preferably, the cell sample is a tumor cell sample. This method comprises (i) obtaining a cellular lysate from a cell sample; (ii) isolating and/or separating proteins from the cell lysate preparation; and (iii) detecting the presence of GEF-H1 phosphovariants. In one embodiment, the detection of GEF-H1 phosphovariants having phosphorylated serine-810 or serine-67, indicates that the cell sample comprises activated PAK4.

In a preferred embodiment, the level of GEF-H1 phosphorylation in this and other methods described herein is determined using whole cells in an ELISA assay using GEF-H1-specific antibodies.

Another aspect of the present invention involves a method ("method 7") for detecting cell proliferation, cell motility and/or cell invasion in a mammal. This method comprises monitoring the phosphorylation level of GEF-H1 at, at least, two timepoints (i.e., timepoint A and at least one other timepoint, B), in a sample taken from the mammal, wherein an increase in the phosphorylation level of GEF-H1 in the sample between the timepoints, is indicative of cell proliferation, cell motility and/or cell invasion.

In a preferred embodiment, the GEF-H1 is a GEF-H1S protein comprising the sequence of SEQ ID NO. 2.

In yet another embodiment, the sample of method 7 is obtained from the mammal's skin, blood, or cells. In one embodiment, the cells are tumor cells.

In another embodiment, the mammal is selected from the group consisting of a human, rat, mouse, dog, rabbit, pig, sheep, cow, horse, cat, primate, goat, or monkey. Most preferably, the mammal is a human.

In another method ("method 8") contemplated by the present invention, peptides comprising the sequence of SEQ ID NO. 3 or 4 are administered to cells or cell lysate preparations to competitively inhibit the phosphorylation of endogenous GEF-H1 proteins. In one embodiment, these peptides are administered in excess, i.e., at such a high concentration that they bind to essentially all PAK4 proteins. In another embodiment, peptides less than 30 amino acids in length that comprise either SEQ ID NO. 3 or SEQ ID NO. 4 are provided. Preferably, these peptides are less than 25 amino acids in length, more preferably less than 20 amino acids in length and most preferably are 18 amino acids in length.

Thus, the present invention also envisages a method ("method 9") for treating cancer in an individual, comprising inhibiting GEF-H1 activity in the individual. In a preferred embodiment, the GEF-H1 is at least one of GEF-H1M, GEF-H1S or GEF-H1U. In a most preferred embodiment, the GEF-H1S comprises the amino acid sequence described in SEQ ID NO. 2.

In another embodiment, the step of inhibiting GEF-H1 activity comprises inhibiting expression of an endogenous gene encoding said GEF-H1. In yet another embodiment, the GEF-H1 activity is inhibited in or near a population of cancerous cells present in said individual. The expression of a gene encoding GEF-H1 may be inhibited or down-regulated by techniques known in the art, such as antisense technology and RNA interference. Accordingly, one may use single- or double-stranded nucleic acids, (i.e., DNA or RNA) in accordance with such methods to bring about disruption, or to terminate translation of, the mRNA transcript associated with a GEF-H1 gene, or by affecting the transcription of a GEF-H1 gene itself.

Another aspect of this invention provides a method ("method 10") for reducing cell proliferation and anchorage-independent cell growth in a cell sample, comprising inhibiting GEF-H1 activity in the cell sample. In one embodiment, the GEF-H1 is at least one of GEF-H1M, GEF-H1S or GEF-H1U. In another embodiment, the GEF-H1 is preferably, GEF-H1S that comprises the amino acid sequence described in SEQ ID NO. 2.

In one aspect of the present invention, an isolated polynucleotide encoding a polypeptide comprising the amino acid sequence of SEQ ID NO. 21, but no other group II PAK amino acids, is provided. In a preferred embodiment, the polypeptide is capable of binding to a guanine-nucleotide exchange factor, whereupon it prevents PAK4-mediated phosphorylation of guanine-nucleotide exchange factor, or reduces the level of PAK4-mediated phosphorylation of guanine-nucleotide exchange factor. In another embodiment, binding of the "SEQ ID NO. 21 polypeptide" to a guanine-nucleotide exchange factor prevents or reduces the level of phosphorylation by any of group II PAK-mediated phosphorylation of the guanine-nucleotide exchange factor to which the polypeptide is bound. In a preferred embodiment, the polypeptide is capable of binding to amino acids 763-921 of GEF-H1S.

According to the present invention, a polypeptide may comprise only parts of SEQ ID NO. 21, as long as that polypeptide can still bind to GEF-H1 isoforms, and as long as the polypeptide does not comprise any other amino acid sequences of the PAK4 protein or of any other group II PAK isoform. Thus, a polypeptide of the present invention may comprise amino acids 276-324 of PAK4 (i.e., SEQ ID NO. 21), or amino acids 280-324, or amino acids 285-324, or amino acids 291-324, or amino acids 298-322 (i.e., SEQ ID NO. 22).

Thus, in one embodiment, the present invention provides an isolated polynucleotide encoding a polypeptide consisting essentially of the amino acid sequence of SEQ ID NO. 21, or consisting essentially of a part of SEQ ID NO. 21. As used herein, the phrase "consisting essentially of" excludes other amino acids of group II PAK proteins except those of SEQ ID NO. 21.

In another embodiment, the isolated polynucleotide encodes a polypeptide consisting of the amino acid sequence of SEQ ID NO. 21.

A polynucleotide encoding SEQ ID NO. 21 may be operably linked to a second polynucleotide that encodes a second protein or polypeptide unrelated to PAK. Thus, the present invention envisions SEQ ID NO. 21-, and SEQ ID NO. 22-DNA constructs that express fusion proteins comprising either or both of SEQ ID NO. 21 and/or SEQ ID NO. 22, and at least one other protein or polypeptide.

In yet another embodiment, the isolated polynucleotide encodes a polypeptide that has at least 70% sequence identity to the amino acid sequence of SEQ ID NO. 21, and wherein the polypeptide is capable of binding to a guanine nucleotide-exchange factor.

In another embodiment, the isolated polynucleotide encodes a polypeptide comprising the amino acid sequence of SEQ ID NO. 22, but no other group II PAK amino acids, is provided. In a preferred embodiment, the polypeptide is capable of binding to a guanine-nucleotide exchange factor, whereupon it prevents or reduces the level of PAK4-mediated phosphorylation of guanine-nucleotide exchange factor. In another embodiment, binding of such a "SEQ ID NO. 22 polypeptide" to a guanine-nucleotide exchange factor prevents or reduces any of group II PAK-mediated phosphorylation of the guanine-nucleotide exchange factor to which the polypeptide is bound.

In another embodiment, the isolated polynucleotide encodes a polypeptide consisting essentially of the amino acid sequence of SEQ ID NO. 22, or consisting essentially of a part of SEQ ID NO. 22. As used herein, the phrase "consisting essentially of" excludes other amino acids of group II PAK proteins except those of SEQ ID NO. 22.

In yet another embodiment, the isolated polynucleotide encodes a polypeptide consisting of the amino acid sequence of SEQ ID NO. 22.

In a further embodiment, the isolated polynucleotide encodes a polypeptide that has at least 90% sequence identity to the amino acid sequence of SEQ ID NO. 22, and wherein the polypeptide is capable of binding to a guanine nucleotide-exchange factor.

In another aspect of the present invention, a polypeptide consisting essentially of the amino acid sequence of SEQ ID NO. 21, is provided. In one embodiment, the polypeptide comprises a label. In another embodiment, the label is selected from the group consisting of biotin, HIS-tag, radiolabel, flurophores, and chromophores.

In yet another aspect of the present invention, a polypeptide consisting essentially of the amino acid sequence of SEQ ID NO. 22 is provided. In one embodiment, the polypeptide comprises a label. In a preferred embodiment, the label is selected from the group consisting of biotin, HIS-tag, radiolabel, flurophores, and chromophores.

The present invention also provides a polypeptide consisting essentially of an amino acid sequence that has at least 70% sequence identity with SEQ ID NO. 21, wherein the polypeptide is capable of binding to a guanine nucleotide-exchange factor.

Further, a polypeptide consisting essentially of an amino acid sequence that has at least 76% sequence identity with SEQ ID NO. 21 is provided, wherein the polypeptide is capable of binding to a guanine nucleotide-exchange factor.

In yet another aspect, a recombinant polypeptide is provided, which comprises an amino acid sequence that has at least 70% sequence identity with the amino acid sequence denoted by residues 276-324 of p21-activated-kinase 4, and at least one other polypeptide sequence, wherein the recombinant polypeptide does not comprise the amino acid sequence denoted by residues 1-275 of p21-activated-kinase 4, nor the amino acid sequence denoted by residues 325-985 of p21-activated-kinase 4. Nor does the recombinant polypeptide comprise any other group II PAK polypeptide sequences.

In one embodiment, the polypeptide comprises a label. In a preferred embodiment, the label is selected from the group consisting of biotin, HIS-tag, radiolabel, flurophores, and chromophores.

Thus, any of the polypeptides of the present invention may be labeled so that they can be detected, easily manipulated or isolated from a sample.

The present invention also provides a polypeptide consisting essentially of an amino acid sequence that has at least 90% sequence identity with SEQ ID NO. 22, wherein the polypeptide is capable of binding to a guanine nucleotide-exchange factor.

In another aspect, a recombinant polypeptide is provided, which comprises an amino acid sequence that has at least 70% sequence identity with the amino acid sequence denoted by residues 298-324 of p21-activated-kinase 4, and at least one other polypeptide sequence, wherein the recombinant polypeptide does not comprise the amino acid sequence denoted by residues 1-297 of p21-activated-kinase 4, nor the amino acid sequence denoted by residues 325-985 of p21-activated-kinase 4. Nor does the recombinant polypeptide comprise any other group II PAK polypeptide sequences.

In a further embodiment, a polypeptide comprising an amino acid sequence that has at least 70% sequence identity with the amino acid sequence denoted by residues 276-324 of p21-activated-kinase 4 is provided. In one embodiment, this polypeptide does not comprise the amino acid sequence denoted by residues 1-275 of p21-activated-kinase 4, and does not comprise the amino acid sequence denoted by residues 325-985 of p21-activated-kinase 4. Nor does the recombinant polypeptide comprise any other group II PAK polypeptide sequences.

In yet another embodiment, a polypeptide comprising an amino acid sequence that has at least 90% sequence identity with the amino acid sequence denoted by residues 298-324 of p21-activated-kinase 4 is provided. In one embodiment, the polypeptide does not comprise the amino acid sequence denoted by residues 1-297 of p21-activated-kinase 4, and does not comprise the amino acid sequence denoted by residues 325-985 of p21-activated-kinase 4. Nor does the recombinant polypeptide comprise any other group II PAK polypeptide sequences.

The present invention also envisions a pharmaceutical composition comprising a polypeptide that consists essentially of, or consists of the amino acid sequence of SEQ ID NO. 21, or part thereof, or SEQ ID NO. 22. In a preferred embodiment, such a polypeptide is capable of binding to a GEF-H1 isoform.

The present invention also provides a method for detecting the presence of a guanine nucleotide-exchange factor in a biological sample. The method comprises:

(i) incubating a biological sample with a p21-activated-kinase-derived polypeptide, and (ii) determining if any of the p21-activated-kinase-derived polypeptide is bound to a guanine nucleotide-exchange factor, wherein (a) the p21-activated-kinase-derived polypeptide comprises an amino acid sequence that has at least 90% sequence identity with the amino acid sequence denoted by residues 298-324 of p21-activated-kinase 4, (b) the p21-activated-kinase-derived polypeptide does not comprise the amino acid sequence denoted by residues 1-297 of p21-activated-kinase 4, and (c) the p21-activated-kinase-derived polypeptide does not comprise the amino acid sequence denoted by residues 325-985 of p21-activated-kinase 4.

In one embodiment, the p21-activated-kinase-derived polypeptide comprises a label. In a preferred embodiment, the label is selected from the group consisting of biotin, HIS-tag, radiolabel, flurophores, and chromophores.

In another embodiment of the method, the step of determining if any of the p21-activated-kinase-derived polypeptide is bound to a guanine nucleotide-exchange factor, comprises removing unbound, radiolabeled p21-activatedkinase-derived polypeptide from the biological sample, and then measuring the level of radioactivity in the sample.

In yet one other aspect of the present invention, is a method of inhibiting PAK4 mediated phosphorylation of a guanine-nucleotide exchange factor. This method comprises exposing a guanine-nucleotide exchange factor to a polypeptide consisting essentially of the amino acid sequence of SEQ ID NO. 21, wherein the polypeptide binds to the guanine-nucleotide exchange factor, thereupon inhibiting some or all of PAK4-mediated phosphorylation of the guanine-nucleotide exchange factor. It is possible that the phosphorylation of GEF-H1 by other group II PAK proteins also can be similarly inhibited by this method.

In one embodiment, the guanine-nucleotide exchange factor is in a biological sample, such as in a tissue, cultured cells, or isolated cells. In another embodiment, the biological sample is obtained from a mammal. In a preferred embodiment, the mammal is a human, mouse, rat, pig, cow, rabbit, dog, cat, horse, goat, primate, or monkey. In a most preferred embodiment, the mammal is a human.

In a further embodiment, the step of exposing the guanine-nucleotide exchange factor to the polypeptide comprises administering to a mammal a pharmaceutical composition that comprises the polypeptide. In a preferred embodiment, the pharmaceutical composition comprising the polypeptide is any one of a tablet, aerosol, powder, liquid, gel, cream, suppository.

The present invention also provides a method for identifying a molecule, which disrupts an interaction between PAK4 and a guanine-nucleotide exchange factor. This method comprises (a) exposing a guanine-nucleotide exchange factor to a polypeptide consisting essentially of the amino acid sequence of SEQ ID NO. 21, wherein the polypeptide binds to the guanine-nucleotide exchange factor to form a complex;

(b) adding one or more test molecules to the complex; and (c) determining whether the polypeptide and the guanine-nucleotide exchange factor are dissociated from one another after the test molecule(s) is added to the complex.

The present invention also encompasses a method of inhibiting PAK4-mediated phosphorylation of a GEF-H1 isoform, comprising introducing into a cell a vector that comprises a polynucleotide, which encodes the polypeptide of SEQ ID NO. 21, wherein the polynucleotide is expressed to produce the polypeptide, and wherein the polypeptide binds to a GEF-H1 isoform in the cell, thereby inhibiting PAK4 phosphorylation. In a preferred embodiment, the vector does not encode any other group II PAK polypeptide sequences.

By "inhibiting" it is understood that all, most, or some of the normal phosphorylation activity of a PAK protein, especially that of PAK4, is reduced when a GID-containing polypeptide is bound to a GEF-H1 isoform. "GID" is defined below.

BRIEF DESCRIPTION OF THE DRAWINGS

FIG. 1: (SEQ ID NOS 32-34 respectively in order of appearance) Direct binding of GEF-H1 to PAK4. Lysates were prepared from 293T cells over expressing (a) myc tagged PAK4 alleles or subdomains and incubated with GST, GST-GEF-H1 (787-921) and GST-Maguin-like bound to Glutathione beads (1,2,3,4 bead designation) or (b) GFP-GEF-H1 and incubated with PAK4 biotinylated peptides (291-355) and (276-324) linked to streptavidin beads. An equivalent amount of beads and excess lysates (500 ug) were used. Eluates of beads and total lysates were analysed by SDS-PAGE and immunoblotted with myc or GEF-H1 antiserum; (c) represents a PAK4 gene schematic outlining the regions of PAK4 used to identify the GEF-H1 interaction domain (GID). d, alignment of the GID defined by the minimal binding region of PAK4 with PAK5 and PAK6.

FIG. 2: The interaction between PAK4 and GEF-H1 occurs in tumour cells. (a) Human tumour cell lysates from A549, HCT116 and H1299 were immunoprecipitated with Protein G beads linked with anti-PAK4, anti-GEF-H1 and anti-PAK4 preimmune sera. Bead eluates were analysed by western blotting using anti-GEF-H1 antiserum. (b) Double immunofluorescence of H1299 cells showing co-localization of PAK4 and GEF-H1 (red) with the cis-golgi associated protein □-COP(green) and partial co-localization with the trans-golgi marker, wheat germ agglutinin (blue).

FIG. 3: (SEQ ID NOS 35-37, 37-45 and 45-47, respectively in order of appearance) PAK4 phosphorylates GEF-H1 in vitro and in vivo. (a) In vitro kinase assay shows that purified GST, GST-GEF-H1(763-921) and GST-Maguin-like protein are phosphorylated by PAK4. The negative control autophosphorylation reaction is the reaction mix without substrate. A concentration gradient of reaction substrate is indicated by the triangles; (b) A weighted PAK4 substrate consensus aligned to phage display hits (above the broken line). Asterisk indicates the phospho-acceptor site. An amino-terminal GEF-H1 peptide (below broken line) with a predicted phosphorylation site is marked with "*"; (c) In vivo phosphorylation of GEF-H1 by PAK4 is demonstrated in a western blot of co-transfected lysates were probed with phosphospecific anti-HA antisera (lower panel). The amount of total GEF-H1 was detected with HA antiserum (upper panel).

FIG. 4: Morphological effects of GEF-H1 alleles. NIH-3T3 cells were transfected with EGFP-tagged GEF-H1 alleles; GEF-H1S (I), GEF-H1SS810A (II), GEF-H1S S67A (III), GEF-H1S S67,810A (IV), GEF-H1 Q312M,R313G (V) and vector EGFP (VI). GFP fluorescence was used to detect expression of GEF-H1 (left panels) and fluorescent-phallicidin was used to monitor cytoskeletal rearrangements (right panels).

FIG. 5: PAK4 regulates lamellipodia formation and stress fibre attenuation through phosphorylation of Ser810. (a) NIH-3T3 cells were transfected with PAK4 and GEF-H1S alleles and examined by fluorescence imaging of EGFP for GEF-H1 alleles, PAK4 constructs were identified by immuno-staining using HA antiserum followed by anti-mouse fluorescent rhodamine conjugate for PAK4 and fluorescent coumarin-Phallicidin to label actin. a, PAK4 (I) and the mutants PAK4 S474E (II) and PAK4 K350,351A (III) co-transfected with the control EGFP. b, GEF-H1S co-transfected with PAK4 alleles as for a, (I-Ill). GEF-H1S S810A, GEF-H1S S67A and GEF-H1S Q312M,R313G together with PAK4 S474E (IV-VI). Arrows highlight lammellipodia induction for cells co-expressing PAK4S474E and GEF-H1S or GEF-H1S S67A. Asterisks mark cells with stress fibres induction. Scale bar represents 10 µm.

FIG. 6: PAK4 signalling through GEF-H1M to the actin and MT cytoskeletons. NIH-3T3 cells were co-transfected with GEF-H1 and PAK4. Expression of GEF-H1 and PAK4 was detected by fluorescence imaging of EGFP for GEF-H1 and PAK4 antiserum (#933) followed with anti-rabbit fluorescent rhodamine for PAK4.Fluorescent coumarin-phallicidin was used in to examine the actin cytoskeleton. Anti-β-tubulin followed by anti-mouse marina blue conjugate was used to stain for the MT cytoskeleton. In (a) GEF-H1M together with PAK4 and the mutant PAK4 S474E are shown. Arrows highlight actin-rich lamellipodia in cells co-expressing GEF-HL M and the mutant PAK4 S474E; (b) GEF-H1M together with vector and the mutants PAK4 S474E and PAK4 K350,351A are shown. Note the non-polarized partial dissolution of the MT cytoskeleton in the presence of the mutant PAK4 S474E Scale bar represents 10 μm.

FIG. 7: Model for reciprocal regulation of Rac and Rho in vivo. (a) GEF-H1 in a non-phosphorylated state retains basal constitutive Rho activity; (b) PAK4 can regulate GEF-H1 by phosphorylation leading to simultaneous Rac activation and inhibition of constitutive Rho signalling.

FIG. 8. (SEQ ID NOS 18, 3, 3, 3, 4, 4 and 4, respectively in order of appearance) Phosphorylation scores of GEF-H1 proteins and peptides. (a) Peptide phospho-isomers derived from potential regulatory regions, used to confirm phosphorylation sites. Residues printed in red are prephosphorylated and block phosphorylation in vitro; (b) A combination of deletion and site-directed mutants used to physically located PAK4 phosphorylation on the GEF-H1 protein.

FIG. 9. (SEQ ID NOS 35, 48-49, 35 and 50-51, respectively in order of appearance) Conservation of GEF-H1 with Cdc24. Conservation of residues with Cdc24 are shaded in pink and yellow. PAK4 phosphorylation sites are highlighted by asterisks on the weighted consensus is which is aligned to the putative regulatory regions conserved with Cdc24.

DETAILED DESCRIPTION OF THE PREFERRED EMBODIMENTS

Figure 10:
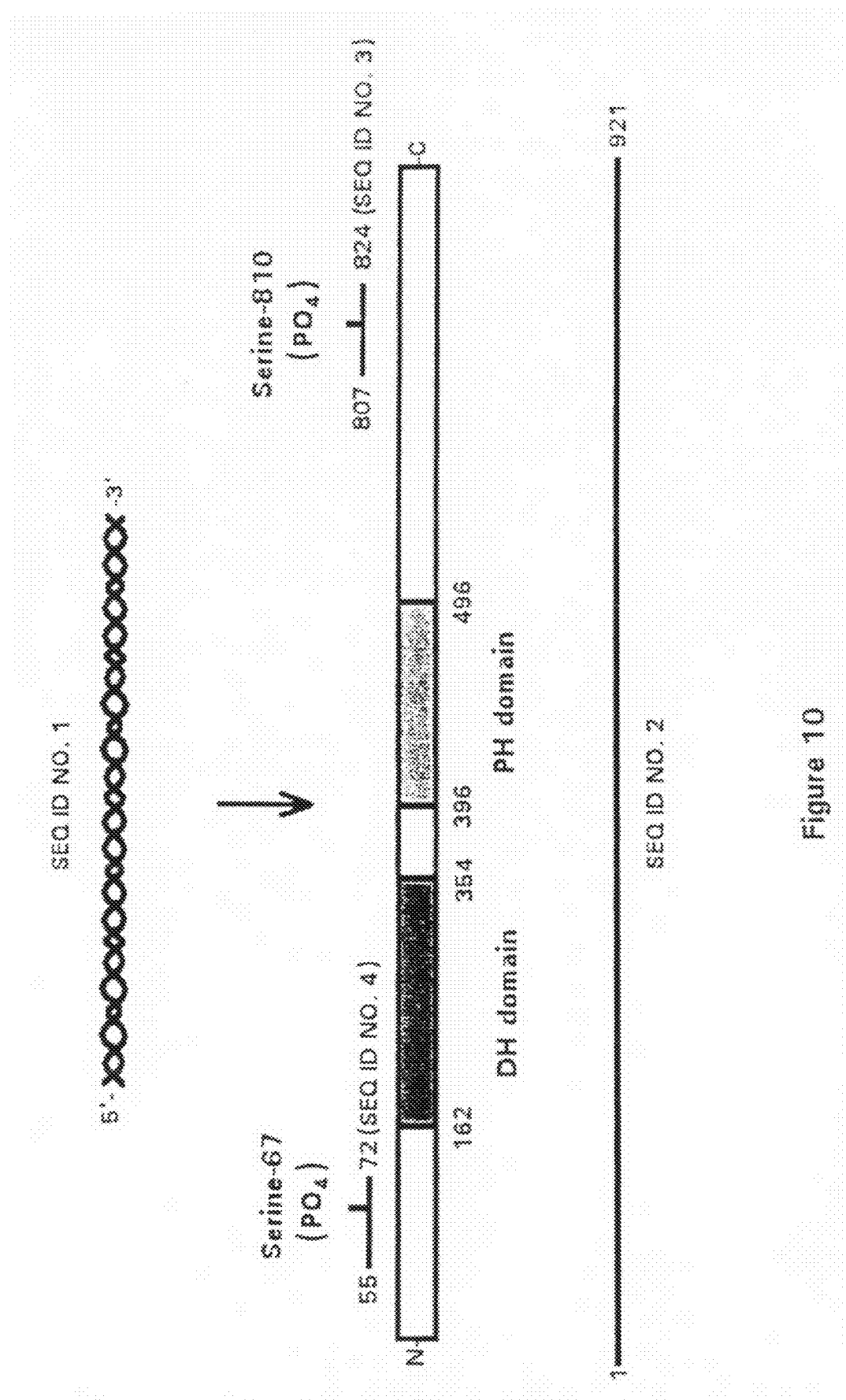
FIG. 10 is a schematic of the GEF-H1S gene, illustrating the positions of phosphorylated serine residues 67 and 810 in relation to key domains of the GEF-H1S protein; the so-called, "DH" domain and the "PH" domain.

In U.S. 60/393,600, various GEF-H1 isoforms were denoted "GEF-H1a," "GEF-H1b," and "GEF-H1c." Those same isoforms are now denoted herein as "GEF-H1M," "GEF-H1S," and "GEF-H1U." Accordingly, "GEF-H1a," is the same as "GEF-H1M"; "GEF-H1b," is the same as "GEF-H1S"; and "GEF-H1c," is the same as "GEF-H1U."

Of these GEF-H1 splice isoforms, GEF-H1S consists essentially of residues 1-921 of GEF-H1, and also contains a 7 amino acid "mini-exon." GEF-H1S does not comprise an N-terminal zinc finger domain. By contrast, the amino acid sequence of GEF-H1M contains a zinc finger domain, which is involved in microtubule binding. The sequence of GEF-H1M is identical to the full length version of GEF-H1, i.e., residues 1-985, described in Krendel et al., supra.

Thus, the present invention provides a novel GEF isoform, "GEF-H1S," that is a biomarker of cell proliferation and a target for screening candidate drugs to treat cancer. The inventors discovered that by detecting a certain phosphorylation state of GEF-H1 isoforms, they could determine whether or not a cell is tumorigenic or shows abnormal cell growth.

GEF-H1 is an guanine nucleotide exchange factor that belongs to the "Dbl family" of exchange factors (Ren et al., *J. Biol. Chem.*, 273(52); 34954-60, 1998). A novel GEF-H1S gene (SEQ ID NO. 1) described herein comprises 2763 nucleotides and encodes a protein (SEQ ID NO. 2) of 921 amino acids that has a predicted molecular weight of approximately 104 kD. Common to all family members, including GEF-H1S, are the "DH" and "PH" domains. See, Chan, et al., *Oncogene*, 9(4):1057-63, 1994; and Musacchio et al., *Trends Biochem. Sci.*, 18(9):343-8, 1993. Typically, enzymatic activity resides in the DH domain which facilitates exchange of GDP to GTP in proteins belonging to the Ras superfamily of Rho GTPases. The DH domain of GEF-H1S (i.e., SEQ ID NO. 2), is located within the amino acids residing at positions 162 and 354 of the GEF-H1S protein. The PH domain is located between amino acids 396 and 496. The present invention also relates to GEF-H1 peptides that do not comprise the DH domain, but do comprise one or more phosphorylation sites.

As described in detail below, cells that overexpress GEF-H1 are anchorage independent and proliferate abnormally. Furthermore, such cells are able to form tumors when implanted into athymic nude mice. Accordingly, one may prevent or reduce the incidence of such a phenotype by downregulating or inhibiting expression of GEF-H1.

The novel GEF-H1S protein having the sequence described in SEQ ID NO. 2, is associated with, and phosphorylated by, the serine/threonine-protein kinase, p-21 activated kinase 4 ("PAK4"). Two regions in the GEF-H1S protein are phosphorylated by PAK4, namely serine-810 and serine-67. "Serine-810" and "serine-67" refer to amino acids at positions 810 and 67 of the GEF-H1S protein, i.e., of SEQ ID NO. 2. However, other GEF-H1 proteins also comprise serine residues at those positions and within the general phosphorylation recognition site. The "phosphorylation recognition site" refers to the short stretch of amino acid residues either side of the phosphorylatable serine/threonine residue that are recognized by a particular kinase. Accordingly, the terms "serine-810" and "serine-67" refer to phosphorylatable serine residues in any one of a number of GEF-H1 proteins. It is conceivable that a threonine residue at those positions (i.e., at positions 810 and 67 of SEQ ID NO. 2) would also be phosphorylated by a kinase.

Thus, any GEF-H1 peptide comprising the denoted serines (bold, underlined) in residues 807-824, RRRSLPAGDALYLSFNPP (SEQ ID NO. 3), and in residues 55-72, RQSLLGSRRGRSSLSLAK (SEQ ID NO. 4), are phosphorylated by PAK4. Other GEF-H1 proteins include GEF-H1M and GEF-H1U. The former is described in Ren et al., *J. Biol. Chem.*, 273(52): 34954-60, 1998; and Krendel et al., *Nat. Cell Biol.*, 4(4): 294-301, 2002. GEF-H1U is described in Reddy & Chatterjee, *Cancer Res.*, 49(7): 1763-7, 1989. The present invention envisions peptides less than 30 amino acids in length that comprise either SEQ ID NO. 3 or SEQ ID NO. 4. Preferably, these peptides are less than 25 amino acids in length, more preferably less than 20 amino acids in length and most preferably are 18 amino acids in length. Accordingly, the present invention also contemplates polynucleotides that encode peptides comprising the sequence of either SEQ ID NOs. 3 or 4. That is, the present invention envisions polynucleotides less than 90 nucleotides in length that encode a peptide comprising the sequence described in SEQ ID NO. 3 or SEQ ID NO. 4. Preferably, the polynucleotide is less than 75 nucleotides in length, more preferably less than 60 nucleotides in length and most preferably 54 nucleotides in length.

Accordingly, serine-810 and serine-67 of these GEF-H1 isoforms will be phosphorylated in the presence of PAK4. Therefore, while the present invention contemplates the measurement of GEF-H1S phosphorylation as an indicator of PAK4 activity, the invention also encompasses the phosphorylation of GEF-H1M and GEF-H1U isoforms. Thus, the "total" GEF-H1 phosphorylation level is indicative of the cumulative phosphorylation states of GEF-H1 proteins comprising a peptide sequence described in SEQ ID NOs 3 or 4; i.e., GEF-H1M, GEF-H1S and GEF-H1U.

This information leads to the prediction that a phosphorylation consensus sequence for GEF-HL is, from N-terminus to C-terminus, "RBSZXG" (SEQ ID NO. 6) or "RBSZXL," (SEQ ID NO. 20), where R is arginine, B is a basic amino acid, S is serine, Z is a hydrophobic amino acid, X is any amino acid, G is glycine, and L is leucine. At some phosphorylation sites in GEF-H1, the C-terminal amino acid residue is a glycine, while at other sites, the residue is a leucine. Accordingly, any peptide comprising this consensus sequence structure is potentially a target for phosphorylation by PAK4, and such peptides can be used in assays according to the present invention. Furthermore, any peptide that consists essentially of the RBSZXG (SEQ ID NO: 6) and/or the RBSZXL (SEQ ID NO: 20) consensus sequences is potentially a target for phosphorylation by PAK4, and such peptides can be used in assays according to the present invention.

PAK4 is overexpressed in human tumor cell lines and, along with other members of the PAK family of kinases, is implicated in the regulation of cell morphology and motility. See, for instance, Callow et al., *J. Biol. Chem.*, 4; 277(1):550-8, 2002; Abo et al., *EMBO J.*, 17(22):6527-40, 1998; Gnesutta et al., *J. Biol. Chem*, 276(17):14414-9, 2001; Qu et al., *Mol. Cell Biol.*, 21 (10):3523-33, 2001; and Dan et al., *J. Biol. Chem.*, 276(34):32115-21, 2001. The "PAK4" protein referred to herein is also described in WO 99/53036 and U.S. Pat. No. 6,013,500. Other PAK enzymes may phosphorylate GEF proteins such as GEF-H1. It is contemplated that PAK5 and PAK6 may phosphorylate a GEF-H1 comprising the phosphorylation sites of SEQ ID NOs. 3 or 4. PAK5 has been described by Pandey et al., *Oncogene*, 21(24): 3939-48, 2002 and Dan et al., *Mol. Cell Biol.*, 22(2): 567-77, 2002. PAK6 is described in Yang et al., *J. Biol. Chem.*, 276(18): 15345-53, 2001.

Overexpression of PAK4 induces localized actin polymerization and the formation of filopedia, and consequently, changes in the actin cytoskeleton of the cell can be attributed to PAK4 activity. Furthermore, PAK kinases have been implicated in oncogenic Ras-driven, anchorage-independent cell growth and in the regulation of cell survival. Callow et al., 2002, for instance, demonstrated that an activated PAK4 has the ability to transform cells, but that the inactive form ("kinase-dead") blocks Ras-dependent, anchorage-independent cell proliferation. In general, tumor cells do not require anchorage and can grow in suspension. Anchorage-independent cell proliferation is a hallmark of tumorigenic cells. Accordingly, PAK4 is strongly implicated in tumorigenesis and that it may be particularly important for Ras transformation.

In that light, studies described herein reveal that GEF-H1 is a substrate for PAK4, and that it is phosphorylated by the activated form of the kinase. Accordingly, by detecting the phosphorylation state of GEF-H1, one is able to determine whether PAK4 is active or inactive. Therefore, one may ascertain whether a cell or tissue sample is proliferating or showing signs of abnormal cell growth or morphology. Thus, GEF-H1 is an excellent biomarker of PAK4 activity and is extremely useful for screening for drugs and compounds that may block PAK4 activity. For instance, a drug that alters the phosphorylation state of GEF-H1 may be one that acts directly or indirectly to inhibit the PAK4 kinase and, thereby, ameliorate, reduce or, ideally, abolish cell proliferation. Therefore, by monitoring the phosphorylation pattern of GEF-H1, in the presence and absence of candidate drugs, one may identify potential cancer therapies.

An assay in this context involves (i) obtaining a cellular lysate from a test sample; (ii) isolating and/or separating proteins from the cell lysate preparation; and (iii) detecting the presence of GEF-H1 phosphovariants, i.e., serine-810 and/or serine-67 phosphorylated GEF-H1 proteins. In this respect, one could determine whether the level of phosphorylation of total GEF-H1 protein in the cell lysate of the test sample is abnormal by comparing that level to the phosphorylation level of total GEF-H1 protein isolated from a control cell sample. A control cell sample is a sample of cells that are of the same cell type as the test sample, but which are isolated from a mammal or from a source that is known to be healthy, i.e., from mammalian wild-type cells. The control cell sample may be isolated from the same individual from whom the test cell sample is isolated. The mammal may be a human, rat, mouse, dog, rabbit, pig, sheep, cow, horse, cat, primate, goat, or monkey.

Thus, the ratio of the level of GEF-H1 phosphorylation between the test and control samples is expected to be greater in test samples that possess either (i) a larger number of active PAK4 kinases or (ii) that possess PAK4 kinase enzymes with a faster rate of catalytic activity. Cells involved in motility, proliferation and cellular invasion, for instance, are likely to have greater PAK4 activity, and therefore, a greater level of GEF-H1 phosphorylation than other types of non-motile cells. In this respect, tumor cells and cells of the immune system (i.e., macrophages) are examples of cells that are involved in motility, proliferation and cellular invasion. Examples of tumor cells include those from cancers of tissues and cancers of hematopoietic origin.

Steps (iii) of the method outlined in the preceding passage can be achieved by using GEF-H1-specific antibodies. Thus, the present invention provides phosphospecific antibodies that target the phosphorylated form of GEF-H1.

To measure the phosphorylation state of GEF-H1, one may employ any one of a number of known protocols. For instance, one may detect phosphospecific antibodies that bind to GEF-H1 or GEF-H1-PAK complexes as described in Example 9 below. A GEF-H1-PAK complex refers to a physical interaction between the GEF-H1 protein and a PAK protein, such that the two proteins are bound to one another. The proteins of the complex may or may not dissociate from one another over a period of time. Preferably, the GEF-H1-PAK complex is a GEF-H1S-PAK4 complex. In this context, the GEF-H1S of the complex comprises the sequence described in SEQ ID NO. 2.

Alternatively, one may measure phosphorylation by engineering a hybrid green fluorescent protein (GFP) to be linked to a single chain antibody that has high affinity for both the phosphorylated and unphosphorylated forms of GEF-H1 peptides represented by SEQ ID NOs. 3 and 4. One would then monitor the extent of "fluorescence quenching" using fluorescence spectroscopy as described by, Deo & Daunert, *Anal. Biochem.*, 289(1): 52-9, 2001. The GFP hybrid undergoes a conformational change upon phosphorylation of the GEF-H1 peptide, thereby producing a different type of fluorescence that is easily and readily detected and quantified.

In a similar vein, a biotinylated peptide substrate derived from the unphosphorylated forms GEF-H1 peptides of SEQ ID NOs. 3 and 4 can be linked to GFP. Subsequent phosphorylation by PAK4 is expected to result in fluorescence quenching as mentioned above. Biotin allows for colorimetric and luminescence measurements where fluorescence cannot be used. For instance, because substances that inhibit PAK4 activity also prevent phosphorylation of the substrate, such as the GEF-H1 peptides, there will be little, or no positive change, in peptide conformation, and consequently little or no change in GFP fluorescence. A biotin label, however, facilitates measurement of phosphorylation, and lack thereof, in the presence of candidate inhibitory substances.

Yet another method useful for measuring the extent of GEF-H1 phosphorylation is "fluorescence resonance energy transfer" (FRET). See Sato et al., *Nat. Biotechnol.*, 20(3): 287-94, 2002. This method measures the transfer of phosphate moieties between the PAK4 phosphorylation recognition domain and the GEF-H1 substrate peptides (or derivatives) (such as those of SEQ ID NOs 3 and 4) as an indicator of phosphorylation.

The gel shift assay is yet another way in which phosphorylation of a protein may be detected. See Wegener et al., *J. Biol. Chem.,* 259(3): 1834-41, 1984.

The present invention uses a biochemical-based cell lysate assay and a radioactive method to monitor, record and detect changes in phosphorylation of total GEF-H1 protein and GEF-H1-derived peptides by PAK4. See Examples 14 and 15 below. In the cellular assay, phosphospecific antibodies to GEF-H1 are used to detect the presence of phosphorylated GEF-H1 in cell lysate preparations. Antibodies that are specific to GEF-H1 can be generated by any one of a number of techniques. For example, antibodies can be produced in rabbits. See, Nims et al., *Lab Anim. Sci.,* 23(3):391-6, 1973. Antibodies can be raised against epitopes that are unique or specific to a particular protein. For instance, one may raise antibodies against the KLH-conjugated peptide CSGDRRRAGPEKRPKSS (SEQ ID NO: 23), as previously demonstrated for PAK4. See, Hashimura et al., *J. Immunol. Methods,* 55(3):375-87, 1982.

Similarly, antibodies specific for GEF-H1 may also generated in rabbits. Specifically, one may raise antibodies against the GEF-H1 regions phosphorylated by PAK4; i.e., to GEF-H1S regions 807-824 (SEQ ID NO. 3) and 55-72 (SEQ ID NO. 4). Antibodies can also be raised to the phosphate-modified versions of these peptides. In such fashion, antibodies that are specific to either the non-phosphorylated or phosphorylated variants of the GEF-H1 can be designed.

By attaching a PAK4 antibody to a surface, such as to the surface of beads, one may trap PAK4 proteins present in lysed cells. Accordingly, any PAK4 proteins present in the cellular lysate will bind to the surface or beads by virtue of their interaction with the surface-/bead-attached antibody. Furthermore, if GEF-H1 is also present in the preparation, GEF-H1/PAK4complexes can be isolated in the same fashion. The cells may be those from established cell lines of known lineage. For example, cell lysates may be prepared from tumor cell lines and subjected to phosphospecific antibody treatment as described above and in Example 14.

An antibody may be a monoclonal or polyclonal antibody, or antibody fragment that has specific binding affinity to a GEF-H1 polypeptide, domain or fragment thereof. "Specific binding affinity" means that the antibody binds to a target polypeptide with greater affinity than it binds to other polypeptides under specified conditions. Preferably, the antibody binds to a GEF-H1 polypeptide comprising the sequence described in any one of SEQ ID NOs. 2, 3 or 4. More preferably the antibody binds to a polypeptide comprising the sequence described in SEQ ID NOs. 3 or 4. Antibodies to GEF-H1 may also bind to phosphorylated variants of GEF-H1 isoforms. Accordingly, these antibodies bind to phosphorylated versions of the peptides described in SEQ ID NOs. 2, 3 and 4. In such fashion, antibodies may be raised that bind to peptides comprising phosphorylated serines, 810 and 67, of the GEF-H1 proteins.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, Kohler et al., *Nature,* 256:495-497, 1975, and U.S. Pat. No. 4,376,110.

An antibody of the present invention includes "humanized" monoclonal and polyclonal antibodies. Humanized antibodies are recombinant proteins in which non-human (typically murine) complementarity determining regions of an antibody have been transferred from heavy and light variable chains of the non-human (e.g. murine) immunoglobulin into a human variable domain, followed by the replacement of some human residues in the framework regions of their murine counterparts. Humanized antibodies in accordance with this invention are suitable for use in therapeutic methods. General techniques for cloning murine immunoglobulin variable domains are described, for example, by the publication of Orlandi et al., *Proc. Nat'l Acad. Sci. USA* 86: 3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immun.* 150:2844 1993.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

An antibody fragment of the present invention includes a "single-chain antibody," a phrase used in this description to denote a linear polypeptide that binds antigen with specificity and that comprises variable or hypervariable regions from the heavy and light chains of an antibody. Such single chain antibodies can be produced by conventional methodology. The Vh and Vl regions of the Fv fragment can be covalently joined and stabilized by the insertion of a disulfide bond. See Glockshuber, et al., *Biochemistry* 1362, 1990. Alternatively, the Vh and Vl regions can be joined by the insertion of a peptide linker. A gene encoding the Vh, Vl and peptide linker sequences can be constructed and expressed using a recombinant expression vector. See Colcher, et al., *J. Nat'l Cancer Inst.* 82: 1191, 1990. Amino acid sequences comprising hypervariable regions from the Vh and Vl antibody chains can also be constructed using disulfide bonds or peptide linkers.

Antibodies of the present invention may be labeled using, for example, fluorescent labels or radioactive labels.

Antibodies or antibody fragments having specific binding affinity to a GEF-H1 or derivative peptide of the invention may be used in methods for detecting the presence and/or amount of that polypeptide in a sample, by (i) probing the sample with the antibody under conditions suitable for target-antibody immunocomplex formation and (ii) detecting the presence and/or amount of the antibody conjugated to the desired polypeptide. Diagnostic kits for performing such methods may be constructed to include antibodies or antibody fragments specific for the target as well as a conjugate of a binding partner of the antibodies or the antibodies themselves.

A "derivative peptide" of GEF-H1 is a peptide comprising an amino acid sequence that is part of the larger, complete GEF-H1 protein. For instance, peptides comprising the sequences described in SEQ ID NOs. 3 and 4 are "derivative peptides" of the GEF-H1 protein.

An antibody or antibody fragment with specific binding affinity to a GEF-H1 or PAK4 polypeptide of the invention can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Antibodies having specific binding affinity to a target polypeptide of the invention may be used in methods for detecting the presence and/or amount of target polypeptide in a sample by contacting the sample with the antibody under conditions such that an immunocomplex forms and detecting the presence and/or amount of the antibody conjugated to the target polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

In another aspect, the invention features a hybridoma which produces an antibody having specific binding affinity to a GEF-H1 polypeptide or a polypeptide domain, where the polypeptide is selected from the group having an amino acid sequence SEQ ID NO. 2. By "hybridoma" is meant an immortalized cell line that is capable of secreting an antibody, for example an antibody to GEF-H1. In preferred embodiments, the antibody to the GEF-H1 comprises a sequence of amino acids that is able to specifically bind a GEF-H1 polypeptide of the invention.

In another aspect, the present invention is also directed to kits comprising antibodies that bind to a polypeptide encoded by any of the nucleic acid molecules described above, and a negative control antibody.

The term "negative control antibody" refers to an antibody derived from similar source as the antibody having specific binding affinity, but where it displays no binding affinity to a polypeptide of the invention.

Also, Western Blot analyses of isolated GEF-H1/PAK4complexes can be prepared and then probed with the aforementioned phosphospecific GEF-H1 antibodies to determine the phosphorylation state of those proteins. Alternatively, the cell lysate may be directly subjected to a Western Blot and the GEF-H1-specific antibodies applied, without prior separation of a specific GEF-H1/PAK4complex.

In any event, identification of a phosphorylated GEF-H1 in a cell sample can be readily and routinely achieved according to the above-described strategy.

A cellular sample may also be treated with a candidate substance such as a drug, chemical, compound, protein, or nucleic acid to determine the effects of that substance upon the activity of PAK4 by monitoring the downstream effects upon GEF-H1 phosphorylation. A candidate substance may "modulate" PAK4 activity, or the interaction between PAK4 and GEF-H1. By "modulate" it is meant that the candidate substance may affect the kinase activity of PAK4 or the extent to which PAK4 and GEF-H1 interact. Accordingly, one effect of "modulation" by a candidate substance is to decrease the level of total GEF-H1 protein phosphorylation in a given sample. It is also conceivable that the candidate substance augments PAK4 kinase activity or facilitates GEF-H1/PAK4interaction. Conversely, the level of total GEF-H1 protein phosphorylation may then be increased after exposure to the substance. Therefore, a candidate substance may modulate PAK4, GEF-H1 or a GEF-H1/PAK4 complex, such that it's effect(s) correlates with the phosphorylation pattern of the GEF-H1 protein.

In assays for screening for substances that modulate PAK4 activity or GEF-H1/PAK4 interaction, one may use the full-length GEF-H1S protein sequence as represented in SEQ ID NO. 2, or a shorter fragment, such as the peptides that are phosphorylated by PAK4 (i.e., those represented by SEQ ID NOs. 3 and 4). Alternatively, a GEF-H1 polypeptide that does not comprise the catalytic, DH domain may also be used to screen for substances that modulate PAK4 activity and/or GEF-H1/PAK4 interaction. Accordingly, the present invention contemplates a GEF-H1 polypeptide that lacks the amino acid region between residues 162 and 354.

A drug screening assay in this context involves (i) obtaining a cellular lysate, preferably from a tumorigenic cell line; (ii) applying to the lysate a candidate substance; (iii) isolating and/or separating proteins from the cell lysate preparation; and (iv) detecting the presence of GEF-H1 phosphovariants. By comparing the level of phosphorylation of total GEF-H1 proteins before and after the candidate substance is applied to a cell or to the cell lysate, it is possible to determine the effect of the candidate substance upon PAK4 activity. Thus, the level of total GEF-H1 protein phosphorylation in such a ratio is expected to fall if the candidate substance is effective in inhibiting PAK4 kinase activity. Further, this ratio (level of GEF-H1 phosphorylation before application of the candidate substance-to-level of GEF-H1 phosphorylation after application of the candidate substance) may also be compared to a "background" level of GEF-H1 phosphorylation in cells and/or cell lysates that have not been treated with the candidate substance. The candidate substance may be applied prior to lysing the cells.

A candidate substance may be peptides that comprise the GEF-H1 sequences of SEQ ID NOs. 3 and 4. Accordingly, when applied to cells at high concentrations, i.e., in excess of the amount of endogenous GEF-H1, the GEF-H1 peptides should compete and bind to endogenous PAK4, thereby inhibiting binding, and phosphorylation of, endogenous GEF-H1. The skilled artisan would know how much of a competitive peptide inhibitor to add in order that the peptide is added to cells or cell lysates "in excess." The candidate substance may also be a nucleic acid that modulates or inhibits expression of PAK4. Thus, antisense polynucleotides or double-stranded RNA molecules may be used according to antisense and RNA-interference techniques to knock out or downregulate PAK4 gene expression.

A successful candidate substance is one that inhibits PAK4, and in so doing, alleviates cellular abnormalities associated with overexpression PAK4. Consequently, a successful candidate substance is one that retards or inhibits cell proliferation, such as that observed in cancerous tissues.

Thus, substances that exert such modulatory or inhibitory effects are useful in modulating or inhibiting cells that (i) proliferate, (ii) possess anchorage-independent growth or (iii) are motile. Accordingly, by administering one or more of these substances to cells exhibiting these properties, one may inhibit proliferation, anchorage-independent growth or cell motility associated with a particular cell sample. Thus, it is possible to treat an individual that has populations of these kinds of cell types by administering one or more of the identified substances in pure or pharmaceutically-formulated forms. According to such rationale, it is possible according to the present invention, to treat an individual that has cancer, or tumorigenic cell growth, by administering a pharmaceutical composition comprising the identified substance that modulates or inhibits one or more cell phenotypes associated with cancerous tissues or cells.

The present invention also makes use of the following PAK4 amino acids sequences as p21-activated-kinase-derived polypeptides, which function in the manner prescribed below.

```
SEQ ID NO. 21:
276-CTPAAPAVPAVPGPPGPRSPQREPQRVSHEQFRAALQLVVDPGDPR
SYLDNF-324

SEQ ID NO. 22:
298-RVSHEQFRAALQLVVDPGDPRSYLD-322
```

Thus, the present invention encompasses a group II p21-activated-kinase-derived polypeptide that is capable of binding to a GEF-H1 protein isoform. It is possible that by binding to the a GEF-H1 protein, such polypeptides can prevent or hinder the docking or binding of full-length, e.g., endogenous PAK4 and other group II PAK family members, to the GEF-H1 protein to which the inventive polypeptide is bound. Examples of group II p21-activated kinases are PAK4, PAK5, and PAK6.

A surprising discovery of the present invention is that a polypeptide comprising only residues 276 to 324 of PAK4 (denoted by SEQ ID NO. 21), can preferentially bind to GEF-H1 family members. This novel binding region, which spans amino acids 276 to 324 of PAK4, also comprises a sequence of amino acids, from residues 298-322 (SEQ ID NO. 22), that is highly conserved between group II PAK proteins. That conserved domain is referred to herein as the "GEF-H1 interacting domain" ("GID"). Amino acids 399 to 454 of PAK5, for instance, have 76% sequence identity with SEQ ID NO. 21, but have 88% sequence identity with the GID domain depicted in SEQ ID NO. 22. Accordingly, the high degree of conservation among group II PAK protein over the GID-region likely means that this region of PAK4, PAK5, and PAK6 can bind to various GEF-H1 family members, such as GEF-H1S, GEF-H1M, and GEF-H1U.

The present invention encompasses any PAK4 polypeptide within the 276-324 stretch of amino acids in SEQ ID NO. 21 that contains the GID region and which still retains the ability to bind to a GEF-H1 isoform. Thus, the present invention encompasses a polypeptide that comprises an amino acid sequence that is only part of the sequence depicted in SEQ ID NO. 21, so long as that polypeptide is capable of binding GEF-H1 isoforms, and does not contain any other PAK4 or other group II PAK protein sequences. Thus, in accordance with the present invention, such a polypeptide does not comprise any other PAK4 amino acid sequences, nor does the polypeptide comprise any other group II PAK polypeptide sequences. For instance, in the case where a polypeptide comprises residues 298-324 of SEQ ID NO. 21, that polypeptide would not comprise amino acid sequences 1-297 or 325-985 of PAK4. However, p21-activated-kinase-derived polypeptides of the present invention may be a part of a fusion protein and be partnered with a non-group II PAK polypeptide or protein.

The present invention also encompasses a polypeptide comprising residues 280-324 of SEQ ID NO. 21, residues 285-324 of SEQ ID NO. 21, residues 291-324 of SEQ ID NO. 21, as well as other variants therefrom. By "variants," it is meant that any sequence within the amino acid sequence depicted in SEQ ID NO. 21 may be used as prescribed by the present invention, so long as that sequence is capable of binding to at least one GEF-H1 isoform.

As explained herein, PAK4 phosphorylation of GEF-H1 reduces or inhibits stress fibre formation and promotes lamellipodia, cell proliferation, and cell motility. Thus, administering an inhibitor of PAK4 phosphorylation, such as a polypeptide that consists essentially of the amino acid sequence of SEQ ID NO. 21, or part thereof, is likely to increase stress fibre formation, making the treated cells less motile, less invasive, and more susceptible to the processes that induce cell apoptosis. For instance, administering a polypeptide comprising the GID domain identified in SEQ ID NOs. 21 and 22, could disrupt cell motility by preventing or reducing phosphorylation of microtubule-bound GEF-H1M. Phosphorylation of GEF-H1M results in its disassociation from the microtubule network. Accordingly, the GID domain-polypeptide could be used to alter the activity of PAK4 on GEF-H1M, thereby disrupting the cell actin infrastructure and cell motility.

A phage display screen was used to identify physiological targets for PAK4 using the kinase domain of PAK4 (amino acids 291-591) fused to GST (Glutathione-S-transferase) as 'bait'. The phage display hits isolated in the screen corresponded to in-frame fusions derived from several distinct genes. One fragment was derived from the Maguin-2-like gene. Two other hits were derived from the GEF-H1S splice variant of GEF-H1. In contrast to GEF-H1M, GEF-H1S lacks a zinc finger region, which was shown to be required for microtubule binding.

To confirm the in vitro interaction of GEF-H1S with PAK4, bacterially expressed GST-fusion proteins were generated with the identical sequences isolated by phage display, encoding either amino acids 763-921 of GEF-H1S or amino acids 385-555 from the Maguin-2-like protein. These fusion proteins were bound to glutathione beads and utilized in binding assays with 293T lysates expressing exogenous PAK4. GST-GEF-H1S (aa763-921), but not GST, nor the Maguin-2-like fragment, was able to bind strongly to both the full-length myc-tagged PAK4 protein and the kinase domain (amino acids 291-591). In contrast, the amino-terminal regulatory domain of PAK4 alone (amino acids 1-309) did not stably interact with GEF-H1S. These results suggest that the interaction is mediated by either a short region N-terminal to the PAK4 kinase domain or by the kinase domain itself.

Biotinylated peptides derived from the N-terminal region of PAK4 sequence were used to further map the GEF-H1 binding site. A peptide consisting of amino acids 276-324 showed strong interaction with GEF-H1S, while another peptide covering a more C-terminal region, amino acids 291-355, did not. Together the results demonstrate that the GEF-H1 interaction domain (GID) is localized between amino acids 276 and 324 of PAK4, such as the region beginning at amino acid 291 and ending at amino acid 322 of PAK4. Sequence alignment of the PAK4 GID with the corresponding domains of the other PAKs revealed significant homology between group-II PAK family members (PAK4, PAK5, and PAK6) in this region. Based on the homology within the GID of PAK4 it is possible that PAK5 and PAK6 also interact with GEF-H1 or related proteins.

Endogenous PAK4 and GEF-H1 stably associate and localize to the Golgi membrane in vivo. To confirm that the in vitro interaction between PAK4 and GEF-H1 is physiologically relevant, co-immunoprecipitation experiments were performed with lysates from A549, HCT116 and H1299 cells with antibodies directed against either PAK4, GEF-H1 or preimmune serum as indicated. The proteins were then analysed by Western blotting using GEF-H1 specific antibodies. Endogenous GEF-H1 protein was detected in complexes immunoprecipitated with either PAK4 or GEF-H1 antibodies but not the preimmune serum. Though the different isoforms of GEF-H1 interact with PAK4 in vivo, in the case of H1299 cells PAK4 interacts more strongly with the smaller GEF-H1 isoform, while in HCT116 cells this preference is not seen.

Earlier studies of PAK4 demonstrated its localization to the Golgi apparatus in the presence of activated Cdc42 resulting in the induction of filopodia. Accordingly, it was determined herein whether endogenous PAK4 and GEF-H1 co-localized in vivo. H1299 cells were stained with antibodies for PAK4 or GEF-H1 together with β-COP antibodies or the trans-Golgi marker, wheat germ agglutinin. PAK4, GEF-H1 and β-COP all localize to the same subcellular region as visualised by fluorescence microscopy. Therefore GEF-H1, like PAK4 is Golgi-membrane associated. The nuclear staining seen with both the PAK4 and GEF-H1 anti-sera is due to the long exposures required for detection of the endogenous proteins and is non-specific. Higher resolution studies show some differences of localization within the Golgi network. For example, PAK4 localizes more to the cis-Golgi membrane and its associated MTs than the trans-Golgi network.

PAK4 Phosphorylates GEF-H1S on Serine 810 In Vitro and In Vivo.

Next examined, was whether GEF-H1 is a PAK4 substrate. In vitro kinase assays were performed using a GEF-H1 GST-fusion protein, a Maguin-2-like GST-fusion protein and GST control protein as substrates for phosphorylation by PAK4. In these assays it was found that the GEF-H1 polypeptide is a high affinity substrate for PAK4 with a Km is the 1 to 5 uM range. PAK4 fails to phosphorylate the GST control and weakly phosphorylated the GST-Maguin-2-like fusion protein.

Previously, it was found that peptides derived from the activation loop sequence of PAK4 are high affinity substrates of PAK4. By examining the ability of PAK4 to phosphorylate a series of peptides highly related to its activation loop, it was possible to deduce a rough substrate consensus for PAK4 (RRXSL(X)nG (SEQ ID NO: 24), where n=1 or 2) that suggested that both the basic residues and the hydrophobic residues flanking the phospho-acceptor site are important for high affinity substrate recognition by PAK4. To further explore the substrate selectivity of PAK4, the sequences of the phage display clones enriched in the PAK4 kinase domain screen were compared with our putative PAK4 substrate consensus. Most of the sequences, including GEF-H1S, contain a region with high similarity to a high affinity PAK4 substrate. Within the GEF-H1 phage display hit that corresponds to GEF-H1S amino acids 763-921, a potential PAK4 phosphorylation site was identified at Ser 810 of GEF-H1S. A peptide derived from the sequence surrounding this site (amino acids 807-824) is also a high affinity substrate for PAK4 with a similar Km for PAK4 as the GST-GEF-H1 (793-921) fusion protein.

Thus, a substrate consensus motif for PAK4 mediated phosphorylation is identified herein as RRXSL(X)$_n$G (SEQ ID NO: 24), where n is "1" or "2" X residues, and "X" is any amino acid.

Various phospho-isomers derived from this peptide were synthesized and tested for their ability to be phosphorylated by PAK4. Peptides with phospho-serine at position 810 were no longer substrates for PAK4. Furthermore, it was confirmed by mutagenesis that Ser 810 of GEF-H1S is the bona fide phosphorylation site for PAK4 in vitro.

While mutation of Ser 810 abolished PAK4 phosphorylation of C-terminal fragments of GEF-H1S, an amino-terminal fragment (amino acids 1-386) of GEF-H1S contained additional PAK4 phosphorylation site(s). Sequence comparison with the PAK4 substrate consensus sequence pointed to Serine residues 57, 66, and 67 as other possible PAK4 phosphorylation sites. By synthesizing peptides corresponding to phospho-isomers of the putative PAK4 phosphorylation sites, it was determined that Ser 67 is the likely in vitro PAK4 phosphorylation site within the amino-terminus of GEF-H1. Interestingly, the PAK4 phosphorylation sites within GEF-H1S are potentially conserved with the sites being either a threonine or a glutamic acid in Cdc24, the yeast Cdc42 GEF that is regulated by the PAK-like kinase Cla4, suggesting the potential importance of these sites. The alignment data indicate that the N-terminal glutamic acid 89 and C-terminal threonine 737 correspond to Ser 67 and 810, respectively in human GEF-H1S.

To confirm that GEF-H1S phosphorylation by PAK4 occurs at these sites in vivo, co-transfection assays were performed and analyzed phosphorylation of GEF-H1 by use of a phospho-specific antibody directed against phospho-serine 810. This antibody is specific for GEF-H1 that is phosphorylated on Ser 810. It was found that Ser 810 is phosphorylated in mammalian cells and that phosphorylation of GEF-H1S on Ser 810 is enhanced in the presence of activated PAK4 as well as wild type PAK4 when co-expressed with Cdc42, whereas in the presence of the kinase-dead mutant and the vector it is not. Expression of the kinase-dead PAK4 is also able to inhibit endogenous PAK4 basal phosphorylation of GEF-H1S on Ser 810. Similarly, phospho-specific antibodies against Ser 67 in GEF-H1S were developed and it was found that not only is Ser 67 phosphorylated in mammalian cells, but also co-transfection of activated PAK4 with GEF-H1S stimulated phosphorylation of Ser 67.

Morphological Changes Mediated by GEF-H1 Alleles.

Nucleotide exchange factors of the Rho GTPase family are involved in the regulation of cytoskeletal structures and cell morphology. The conserved Dbl homology (DH) and pleckstrin homology (PH) domains are critical for function of these exchange factors. GEFs have been analysed for their ability to stimulate exchange on Rho GTPase substrates in vitro or by their over-expression in vivo. In the case of GEF-H1, various groups have shown catalytic activity on Rac and Rho. Transient expression of GEF-H1 in Cos-7 cells and isolated expression of the GEF-H1 DH-PH domains shows activity towards Rac in vivo and in vitro respectively. Analysis by in vitro and in vivo assays in Cos-1 and HeLa cells showed measurable activities on Rho for GEF-H1 which is in agreement with a previous study.

Table 1 shows the effect of GEF-HL mutants on fibroblast morphology; and Table 2 shows the effect of PAK4 regulation of GEF-H1 on fibroblast morphology.

To analyse the effect of GEF-H1 on cell morphology in fibroblasts, EGFP (enhanced green fluorescent protein) fusion constructs of GEF-H1S and a series of mutant alleles of the PAK4 phosphorylation sites in GEF-H1S were introduced into NIH3T3 cells. Also constructed, was a dominant negative allele by mutating the DH domain of GEF-H1 resulting in GEF-H-QR312,313MG. In a p21-binding domain (PBD) assay this dominant-negative allele inhibited accumulation of Rac-GTP but not Cdc42-GTP in NIH-3T3 cells. The actin cytoskeleton was stained with coumarin-phallicidin to contrast F-actin structures of EGFP fluorescing cells by microscopy.

Wild type GEF-H1S typically localized to the perinuclear region and cells appeared elongated with occasional stress fibres. By contrast over-expression of GEF-H1S-S810A alone lead to an accumulation and disorganized array of stress fibres compared to non-transfected cells. The induction of stress fibres is striking given the relatively modest effects on the actin cytoskeleton upon expression of either wild type GEF-H1S or PAK4 alleles alone. The morphology of GEF-H1S-S67A expressing cells was similar to the morphology of cells expressing the dominant negative GEF-H1S DH mutant. Expression of the DH domain mutant GEF-H1S-QR312, 313MG, creates a trail of wildly distributed cytoplasmic extensions. The induction of stress fibres in the case of GEF-H1S-S810A is reminiscent of Rho activation, while the disorganized cytoplasmic extensions seen with GEF-H1-Q312R,M313G and GEF-H1S-S67A could be remnants of non-retracted cell tails that might be due to Rho inhibition. The changes in localization and the actin cytoskeleton is especially dramatic in the double mutant of GEF-H1S-(S67A-S810A). Cytoplasmic aggregates of F-actin were found in EGFP-GEF-H1S (S67A-S810A) expressing cells, as well as wide-arcing lamella devoid of F-actin. The redistribution of the phosphorylation-site mutant proteins and inappropriate accumulation of cytoplasmic F-actin, supports the idea that localization is critical for the ability of GEF-H1 to stimulate stress fibres.

Activated PAK4 and GEF-H1S Induce Lamellipodia Formation in NIH-3T3 Cells.

Induction of F-actin structures in fibroblasts, namely the formation of filopodia, lamellipodia, and stress fibres is due to signalling by the active forms of Cdc42, Rac, and Rho, respectively. Because PAK proteins and specifically PAK4 play a role in regulating F-actin based morphological structures, experiments were devised to determine whether PAK4-induced changes in cell morphology were mediated by regulation of GEF-H1S. Also co-expressed were EGFP-GEF-H1S constructs with various HA epitope-tagged PAK4 alleles in NIH-3T3 cells. Exogenous PAK4 was detected with an anti-HA antibody (red) and the actin cytoskeleton was stained with coumarin-phallicidin (blue). Although NIH-3T3 cells have low but detectable levels of endogenous PAK4 and GEF-H1 these were not activated under the conditions of the experiment.

By employing various alleles of PAK4 it was possible to confirm which morphological effects were driven through PAK4 phosphorylation of GEF-H1. Co-expressing the PAK4 alleles with the EGFP control produced relatively modest effects on the formation of F-actin based structures in NIH-3T3 cells. In cells co-expressing wild-type PAK4 together with wild-type GEF-H1S, a dramatic increase in filopodia was observed, in contrast to either PAK4 or GEF-H1S expressed alone. The filopodial structures seemed to be dependent on the lower activity of the wild type PAK4 allele and the interaction with GEF-H1S since they were not observed when either protein was expressed in cells alone or in vector co-transfected controls. In cells co-expressing the activated PAK4 S474E and GEF-H1S, these structures transitioned from filopodia to lammellipodia at the leading edge. Neither filopodia nor lammellipodia were observed when GEF-H1S was transfected together with the kinase inactive PAK4 K350,351A however stress fibres were now abundantly present. Taken together with our analysis of the PAK4 phosphorylation site mutants in GEF-H1S, this suggests that PAK4 kinase activity is responsible for the transition to lamellipodia formation.

To confirm whether the formation of these structures is dependent on the ability of PAK4 to phosphorylate GEF-H1S, the phosphorylation site mutants of GEF-H1S were used. Co-transfection of a mutant GEF-H1S-S810A allele together with PAK4 S474E shows a profusion of stress fibres. This, together with the result from the kinase-dead allele, suggests that phosphorylation of Ser 810 is responsible for both the signals that lead to lamellipodia formation and inhibition of stress fibre formation in fibroblasts. Additionally, PAK4 S474E and GEF-H1S S810A localized to distinct peripheral sites reminiscent of cell adhesion attachment sites that serve as nucleation points for actin stress fibres. This type of localization of GEF-H1 has also been seen in HeLa cells. Conversely to the effects seen by mutation of S810, co-expression of mutant GEF-H1S-S67A with activated PAK4-S474E allows GEF-H1 dependent formation of lamellipodia while preventing stress fibre formation. Our experiments do not address the qualitative difference between the lamellipodia derived from the non-mutant GEF-H1S and mutant GEF-H1S S67A.

Exchange activity of GEF-H1 is achieved through the interaction of the Dbl homology (DH) domain with the Rac or Rho GTPases in their inactive state. To determine whether GEF-H1S mediated effects driven by PAK4 phosphorylation are dependent upon GEF-H1S exchange activity NIH-3T3 cells co-expressing the GEF-H1S dominant negative DH mutant (Q312M,R313G) with various alleles of PAK4 were examined. Wide-arcing lamella lacking actin were observed, which is in contrast to the actin rich lamellipodia or stress fibres formed in the presence of active alleles of GEF-H1S and activated PAK4. The result confirms that PAK4 signals are relayed directly through the exchange activities of GEF-H1. A previous study of GEF-H1 showed constitutive lamellipodia induction in Cos-7 cells by over-expression of GEF-H1. It was shown, therefore, that by the addition of an activated PAK4/GEF-H1S complex it was possible to reconstitute this effect in NIH-3T3 cells.

Effects of PAK4 Through GEF-H1M on Cell Morphology

Residues phosphorylated by PAK4 in GEF-H1S are conserved in the MT ("microtubule") bound form of GEF-H1, "GEF-H1M." GEF-H1M contains a zinc finger domain in its amino terminus that allows it to bind to microtubules. The role microtubule binding in determining the ability of PAK4 to control GEF-H1M activity was investigated. Studies were performed with GEF-H1M that allowed simultaneous examination of both MT (through EGFP-GEF-H1M labelling of MTs in vivo) and actin cytoskeleton (through F-actin staining with coumarin-phallicidin). Also studied, were changes in the MT cytoskeleton by co-staining with β-tubulin antibodies.

In the case of F-actin based morphological changes, the splice isoforms of GEF-H1 show some differences in their effects. Unlike GEF-H1S which gave occasional distributed stress fibres, cells overexpressing GEF-H1M often displayed stress fibres at the cell periphery that gave the appearance of a woven halo of F-actin suggesting that some Rho stimulating activity may be locally restricted to the MT ends. The absence of filopodial induction was another discernable difference between GEF-H1M and GEF-H1S when co-expressed GEF-H1M with wild type HA tagged PAK4. In this instance, no filopodia are seen. Similar to GEF-H1S, the transition to lammellipodia however, was observed when co-expressed with activated PAK4-S474E.

Consistent with reports in the literature GEF-H1M like LFC (murine GEF-H1), was stably associated with microtubules. Over-expression of GEF-H1 is known to stabilize microtubules in vivo. Stabilization of MTs is apparent by their radial alignment as seen in cells expressing EGFP-GEF-H1M alone or when co-expressed with either wild type or kinase dead PAK4. However, co-expression of activated PAK4 with EGFP-GEF-H1M results in the destabilizing of MTs and the remarkable redistribution of GEF-H1M from MTs to the cytoplasm. MT polarity is also clearly altered in cells co-expressing GEF-H1M with the different alleles of PAK4. These results taken together with the findings of the present invention show that PAK4 can control the cross-talk mediated by GEF-H1 between the actin cytoskeleton and the MT network.

SEQ ID NO. 1
atgcctgtaacaagagcatcacagccaaggaagccctcatctgcccaaca
acagaaagcggccctgctgaagaacaacaccgccttgcagtccgtttctc
ttcgaagtaagacaaccatcccgggagcggccaagctcggccatctacccc
tccgacagcttccggcagtccctcctgggctcccgccgtggccgctcctc
cttgtctttagccaagagtgtttctaccaccaacattgctggacatttca
atgatgagtctcccctgggctgcgccggatcctctcacagtccacagac
tccctcaacatgcggaaccgaaccctatccgtggaatccctcattgacga
agcagaggtaatctacagtgagctgatgagtgactttgagatggatgaga
aggactttgcagctgactcttggagtcttgctgtggacagcagcttcctg
cagcagcataaaaaggaggtgatgaagcagcaagatgtcatctatgagct
aatccagacagagctgcaccatgtgaggacactgaagatcatgacccgcc
tcttccgcacggggatgctggaagagctacacttggagccaggagtggtc
cagggcctgttccctgcgtggacgagctcagtgacatccatacacgctt
cctcagccagctattagaacgccgacgccaggccctgtgcctggcagca
cccggaactttgtcatccatcgctttgggtgatctgctcatcagccagttc
tcaggtcctagtgcggagcagatgtgtaagacctactcggagttctgcag
ccgccacagcaaggccttaaagctctataaggagctgtacgcccgagaca
aacgcttccagcaattcatccggaaagtgacccgccccgccgtgctcaag
cggcacggggtacaggagtgcatcctgctggtgactcagcgcatcaccaa
gtaccgttactcatcagccgcatcctgcagcattcccacgggatcgagg
aggagcgccaggacctgaccacagcactggggctagtgaaggagctgctg
tccaatgtggacgagggtatttatcagctggagaaaggggcccgtctgca
ggagatctacaaccgcatggaccctcgggcccaaaccccagtgcctggca
agggccccttttggccgagaggaacttctgaggcgcaaactcatccacgat
ggctgcctgctctggaagacagcgacggggcgcttcaaagatgtgttagt
gctgctgatgacagatgtactggtgtttctccaggaaaaggaccagaagt
acatctttcctaccctggacaagccttcagtggtatcgctgcagaatcta
atcgtacgagacattgccaaccaggagaaagggatgtttctgatcagcgc
agcccccacctgagatgtacgaggtcacacagcatcccgggatgaccgga
gcacctggatccgggtcattcagcagagcgtgcgcacatgcccatccagg
gaggacttcccctgattgagacagaggatgaggcttacctgcggcgaat
taagatggagttgcagcagaaggaccgggcactggtggagctgctgcgag
agaaggtcgggctgtttgctgagatgacccatttccaggccgaagaggat
ggtggcagtgggatggccctgcccaccctgcccaggggcctttccgctc
tgagtcccttgagtccctcgtggcgagcggctgctgcaggatgccatcc
gtgaggtggagggtctgaaagacctgctggtggggccaggagtggaactg
ctcttgacaccccgagagccagccctgcccttggaaccagacagcggtgg
taacacgagtcctggggtcactgccaatggtgaggcagaaccttcaatg
gctccattgaactctgcagagctgactcagactctagccagagggatcga
aatggaaatcagctgagatcaccgcaagaggaggcgttacagcgattggt caatctctatggacttctacatggcctacaggcagctgtggcccagcagg
acactctgatggaagcccggttccctgagggccctgagcggcgggagaag
ctgtgccgagccaactctcggatggggaggctggcagggctggggctgc
ccctgtggcccctgaaaagcaggccacggaactggcattactgcagcggc
aacatgcgctgctgcaggaggagctacggcgctgccggcggctaggtgaa
gaacgggcaacccaagctggcagcctggaggcccggctccgggagagtga
gcaggcccgggcactgctggagcgtgaggccgaagaggctcgaaggcagc
tggccgccctgggccagaccgagccactcccagctgaggcccctgggcc
cgcagacctgtggatcctcggcggcgcagcctccccgcaggcgatgccct
gtacttgagtttcaacccccccacagcccagccgaggcactgaccgcctgg
atctacctgtcactactcgctctgtccatcgaaactttgaggaccgagag
aggcaggaactggggagccccgaagagcggctgcaagacagcagtgaccc
tgacactggcagcgaggaggaaggtagcagccgtctgtctccgccccaca
gtccacgaggtgagaccctggcggagacatggaccagagactttaccaga
atgcaggacatcccggaggagacggagagccgcgacggggaggctgtagc
ctccgagagctaa SEQ ID NO. 2
MPVTRASQPRKPSSAQQQKAALLKNNTALQSVSLRSKTTIRERPSSAIYP
SDSFRQSLLGSRRGRSSLSLAKSVSTTNIAGHFNDESPLGLRRILSQSTD
SLNMRNRTLSVESLIDEAEVIYSELMSDFEMDEKDFAADSWSLAVDSSFL
QQHKKEVMKQQDVIYELIQTELHHVRTLKIMTRLFRTGMLEELHLEPGVV
QGLFPCVDELSDIHTRFLSQLLERRRQALCPGSTRNFVIHRLGDLLISQF
SGPSAEQMCKTYSEFCSRHSKALKLYKELYARDKRFQQFIRKVTRPAVLK
RHGVQECILLVTQRITKYPLLISRILQHSHGIEEERQDLTTALGLVKELL
SNVDEGIYQLEKGARLQEIYNRMDPRAQTPVPGKGPFGREELLRRKLIHD
GCLLWKTATGRFKDVLVLLMTDVLVFLQEKDQKYIFPTLDKPSVVSLQNL
IVRDIANQEKGMFLISAAPPEMYEVHTASRDDRSTWIRVIQQSVRTCPSR
EDFPLIETEDEAYLRRIKMELQQKDRALVELLREKVGLFAEMTHFQAEED
GGSGMALPTLPRGLFRSESLESPRGERLLQDAIREVEGLKDLLVGPGVEL
LLTPREPALPLEPDSGGNTSPGVTANGEARTFNGSIELCRADSDSSQRDR
NGNQLRSPQEEALQRLVNLYGLLHGLQAAVAQQDTLMEARFPEGPERREK
LCRANSRDGEAGRAGAAPVAPEKQATELALLQRQHALLQEELRRCRRLGE
ERATEAGSLEARLRESEQARALLEREAEEARRQLAALGQTEPLPAEAPWA
RRPVDPRRRSLPAGDALYLSFNPPQPSRGTDRLDLPVTTRSVHRNFEDRE
RQELGSPEERLQDSSDPDTGSEEEGSSRLSPPHSPRGETLAETWTRDFTR
MQDIPEETESRDGEAVASES

SEQ ID NO. 3
RRRSLPAGDALYLSFNPP

SEQ ID NO. 4
RQSLLGSRRGRSSLSLAK

SEQ ID NO. 5
RGETLAETWT

-continued

SEQ ID NO. 6
RBSZXG

SEQ ID NO. 7
CPRRRSLPAGDALYLSFNPP

SEQ ID NO. 8
CRQSLLGSRRGRSSLSLAK

SEQ ID NO. 9
CRQSLLGSRRGRSSLSLAK

SEQ ID NO. 10
TGTAGATCCTCGGCGGCGCGCTCTCCCCGCA

SEQ ID NO. 11
GGTGATGCCCATGGTCTCCAGCAGGAT

SEQ ID NO. 12
ATCCTGCTGGTGACCATGGGCATCACCA

SEQ ID NO. 13
GCCGTGGCCGCTCCGCCTTGTCTTTA

SEQ ID NO. 14
TAAAGACAAGGCGGAGCGGCCACGGC

SEQ ID NO. 15
QRITKY

SEQ ID NO. 16
GCAGAATTCTGTAACAAGAGCATCACA

SEQ ID NO. 17
GCGCTCGAGTTAGCTCTCGGAGGCTACAGCCT

SEQ ID NO. 18
RRKSLVGTPYWMAPE

SEQ ID NO. 19
biotin-LC-LC-RRKSLVG(pT)PYWMAPE

SEQ ID NO. 20
RBSZXL

SEQ ID NO. 21
CTPAAPAVPAVPGPPGPRSPQREPQRVSHEQFRAALQLVVDPGDPRSYLD
NF

SEQ ID NO. 22
RVSHEQFRAALQLVVDPGDPRSYLD

EXAMPLES

Example 1

Cloning of GEF-H1S

Primers MC1 GCAGAATTCTGTMCMGAGCATCACA (SEQ ID NO. 16) and MC3b GCGCTCGAGT-TAGCTCTCGGAGGCTACAGCCT, (SEQ ID NO. 17) designed from Accession No. KIAA0651, deposited at the NCBI (National Center for Biotechnology Information, USA) were used in a polymerase chain reaction (PCR) to amplify the GEF-H1S gene from a human whole brain plasmid cDNA library (Clontech laboratories Cat #HL9002CC). Twenty-rounds of PCR were performed using EXPAND polymerase (Roche Molecular, USA Cat #1681834). The primer MC1 introduced an EcoR1 restriction enzyme site in the 5' position and MC3b contains a Xho1 restriction enzyme site in the 3' position. The sequences of the restrictions enzymes sites are not part of the native GEFH-1b sequence. The resultant PCR product was inserted into an EcoR1 and Xho1 restriction-digested plasmid vector, pcDNA (Invitrogen Cat #V790-20) backbone with a modified multiple cloning site. The GEF-H1S gene was then excised using the restriction enzymes HindIII and Xba1 and inserted into a similarly restricted expression vector, pRSV/Rc (Promega, USA).

Example 2

Expression and Anchorage Independent Proliferation

A stably expressing clone designated 192.58 containing GEF-H1S was established in the mouse fibroblast cell line, NIH-3T3. The pRSV/Rc subcloned vector expresses the GEF-H1S protein in tissue culture cells.

The GEF-H1S clones were plated in tissue culture vessels which prevent adherence. Cells over-expressing GEF-H1S are anchorage independent. NIH3T3 cells harboring only the vector expression vector pcDNA did not transform spontaneously when anchorage was prevented. Only the clones harboring the GEF-H1S gene were shown to survive and proliferate. Therefore, expression of GEF-H1S allows for anchorage independent survival and proliferation of NIH-3T3 cells. The ability for cells to proliferate was measured using the tetrazolium salt XTT based assay (Roche Molecular Biochemicals Cat #1465015) which measured only metabolically active cells in culture. Measurements were made over a time course.

Example 3

Effect of GEF-H1S on a Mouse Tumor Model

The 192.58 cells formed tumors when transferred into athymic nude mice. Eight mice per group were injected subcutaneously with NIH-3T3 cells harboring either a control pcDNA expression vector or pcDNA expression vector expressing the GEF-H1S gene. Palpable tumors were measured in mice treated with the 192.58 cells over a time course. No palpable tumors were detected in mice implanted with cells harboring pcDNA expression vector.

Example 4

GEF-H1S is a Substrate for PAK4

The reagents used specifically for recovery of the first GEF-H1S polypeptide was an expression plasmid pGEX-4T (Amersham Biosciences Cat #27-4581-01) harboring a polypeptide of the catalytic domain of PAK4 representing amino acids 291 to 591. This expression vector allowed production and expression of a gene appropriately inserted, as a fusion protein where the fusion partner is the protein product of the SJ26 gene glutathione-s-transferase (GST). The fusion partner GST allows for affinity immobilization on glutathione sepharose 4B matrix (Amersham Biosciences Cat #17-0756-01) also known as glutathione beads. The PAK4 polypeptide immobilized to these beads was incubated with a lysate containing phage particles expressing a library of peptides derived from MCF7 (breast carcinoma tissue culture cells available from ATCC, USA) cDNA. See, Zozulya et al., *Nat. Biotechnol.*, 17(12): p. 1193-8, 1999. Upon sequencing many of the candidates obtained in this screen, the GEF-H1S polypeptide was discovered in the clone designated 13-8. Sequencing was performed on a ABI prism machine using standard methods provided by the manufacturer (Applied Biosystems, USA).

Example 5

PAK4 is Able to Phosphorylate GEF-H1S In Vitro

The cDNA encoding GEF-H1S obtained in the phage display screen was excised and subcloned into pGEX-4T expression vector to allow for recombinant production of protein for in vitro experiments. The GEF-H1S protein was then mixed with PAK4 kinase and incubated such that PAK4 phosphorylated the GEF-H1S. A portion of this kinase reaction was separated by SDS-PAGE and autoradiographed to visualize the extent of phosphorylation. The autoradiograph showed phosphorylation of the GEF-H1S polypeptide and no phosphorylation of the fusion partner GST. SDS-PAGE is a universal protein separation and visualization technique that is described in Laemmli, *Nature*, 227(259):680-5, 1970.

Example 6

Serine 810 and Serine 67 of GEF-H1S is Phosphorylated by PAK4 In Vitro

From the phosphorylation experiments described above, two peptides of GEF-H1S were identified as being targets for PAK4-induced phosphorylation. The GEF-H1S target residues were identified by aligning the PAK4 activation loop peptide with the GEF-H1S polypeptide sequence amino acids 762 to 921. In vitro kinase assays subsequently showed that GEF-H1S peptides PRRRSLPAGDALYLSFNPP (SEQ ID NO.45) and RQSLLGSRRGRSSLSLAK (SEQ ID NO. 4) are phosphorylated by PAK4.

The extent of phosphorylation of these peptide substrates was compared visually by autoradiography and a consensus of substrate phosphorylation empirically determined. A consensus sequence could predicted to be, for instance, RBSZX [G/L] (SEQ ID NO: 25), where R is the amino acid arginine; B is any basic amino acid; S is the amino acid serine; Z is any hydrophobic amino acid; X is any amino acid, G is glycine and L is leucine. Identification of the amino acid residue was performed by kinase assay using PAK4 as the enzyme and isomers of predicted substrate regions of GEF-H1S.

The following phosphoisomers (phosphate-modified GEF-H1S peptides) were used in PAK4 kinase assays to determine which residues were specifically phosphorylated. Because certain residues were modified to comprise a phosphate moiety (the underlined residues below), they could not be phosphorylated by PAK4. These results revealed that serines 810 and 67 of GEF-H1S are phosphorylation sites for PAK4.

Example 7

GEF-H1S Interacts with PAK4

Additional evidence that GEF-H1S is a substrate for PAK4, was obtained using the GST immobilization technique described above to show interaction of GST-immobilized GEF-H1S with different alleles of PAK4 expressed in 293T cells. Immunoprecipitation techniques both for protein affinity and antigen antibody mediated immunoprecipitation are described in Lew et al., *J. Immunol. Methods*, 136(2):211-9, 1991; and Anderson et al., *Methods Enzymol.*, 96:111-20, 1983.

The GST immobilized GEF-H1S polypeptide was used to conduct immunoprecipitation from the 293T cell extracts. The resulting protein complexes on the beads were identified by separating on SDS-PAGE followed by Western blotting to identify proteins that are present. The Western blot technique (Renart et al., *Methods Enzymol.*, 104:455-60, 1984) is universally used to identify proteins using specific immunoreagents like antibodies. The PAK4 protein was fused to this myc affinity tag, Cravchik et al., *Gene*, 137(1):139-43, 1993, and PAK4 alleles were shown to be present using the monoclonal antibody specific for the myc affinity tag. The detection of PAK4 after immunoprecipitation with the immobilized GEF-H1S on the GST beads showed a physical interaction between these two proteins in a solution of cellular proteins. PAK4 was not present after immunoprecipitation with immobilized fusion partner GST. This interaction was limited by the presence or absence of GEF-H1S.

Example 8

GEF-H1S as a Mechanism-Based Biomarker for PAK4 Kinase Activity in Tumors

Antibodies specific for PAK4 were generated in rabbits by immunizing rabbits with the KLH conjugated peptide CSGDRRRAGPEKRPKSS (SEQ ID NO: 23), which is part of the PAK4 protein, conjugated to KLH. See, Nims et al., 1973. 23(3):391-6; and Hashimura et al, 1982. Antibodies specific for GEF-H1 were also generated in rabbits by immunizing with the GST-GEF-H1S polypeptide which comprises amino acids 762 to 921.

The PAK4 antibody serum was linked (by interaction of the Fc portion of the immunoglobulin of the IgG isotype to Protein G of *S. Aureus*) to Protein G beads (Roche molecular, USA Cat #124 3233). The PAK4 antibody laden beads where mixed with cellular lysates of three human tumor cell lines

| Identifier | | Peptide sequence | Region of protein |
|---|---|---|---|
| 681 | (SEQ ID NO. 18) | RRKSLVG<u>T</u>PYWMAPE | PAK4 activity loop |
| 1008 | (SEQ ID NO. 3) | RRRSLPAGDALYL<u>S</u>FNPP | GEF-H1 (807-824) |
| 1009 | (SEQ ID NO. 3) | RRR<u>S</u>LPAGDALYLSFNPP | GEF-H1 (807-824) |
| 1010 | (SEQ ID NO. 3) | RRRSLPAGDAL<u>Y</u>LSFNPP | GEF-H1 (807-824) |
| 1412 | (SEQ ID NO. 4) | RQSLLGSRRGRS<u>S</u>LSLAK | GEF-H1 (55-72) |
| 1413 | (SEQ ID NO. 4) | RQSLLGSRRGR<u>S</u>SLSLAK | GEF-H1 (55-72) |
| 1414 | (SEQ ID NO. 4) | RQ<u>S</u>LLGSRRGR<u>S</u>SLSLAK | GEF-H1 (55-72) |

A549, HCT116 and H1299 (ATCC, USA). The resulting immunoprecipitate was separated on SDS-PAGE and subjected to western blot. The GEF-H1 specific antibody was shown to immunoprecipitate endogenous GEF-H1. This result confirms the presence of GEF-H1S in the three tumor cell lysates. The interaction of endogenous PAK4 was demonstrated by the detection of endogenous GEF-H1 in the Western Blot when probed with the GEF-H1 specific antibody. The interaction is limited by the presence and absence of PAK4.

Example 9

GEF-H1S Phosphospecific Antibodies are a Tool for Monitoring PAK4 Kinase Activity in Tumors KLH conjugates peptides CPRRR<u>S</u>LPAGDALYLSFNPP (SEQ ID NO. 7), CRQSLLGSRRGR<u>SS</u>LSLAK (SEQ ID NO. 8) and CRQSLLGSRRGR<u>SS</u>LSLAK (SEQ ID NO. 9) were used to generate antibodies in rabbits. The bold, underlined serine residues, "S," denote residues modified by phosphate. "Anti-1009" is an antibody that detects GEF-H1 protein phosphorylated at serine-810 of SEQ ID NO. 7. Antibodies that are raised against peptides comprising the sequences described in SEQ ID NOs. 8 and 9, recognize the serine-67 phosphorylated forms of the GEF-H1 peptides.

The ability of the anti-sera to recognize serine-810 phosphorylated GEF-H1S protein was demonstrated in an experiment where 293T cells (ATCC, USA) were transiently transfected to simultaneously express GEF-H1S and different alleles of PAK4.

In this experiment GEF-H1S expression vector was pRSV/Rc and the PAK4 expression vector was pcDNA. Lysates were prepared from the transfected 293T cells and analyzed by Western Blot using the anti-1009 reagent. The results demonstrate a marked increase in phosphorylated GEF-H1S above the basal phosphorylation (means a portion of the GEF-H1S is already phosphorylated by the endogenous kinase) in the presence of wild type PAK4 (1-591) and PAK4 mutant, S474E, and a marked decrease in the level of phosphorylation in the presence of PAK4 kinase dead K350,351A. These phosphospecific antibodies can be used to detect PAK4 activity in tumors by virtue of its specific phosphorylation of GEF-H1.

Example 10

Construction of GEF-H1S Alleles

The following list refers to alleles representing wild type, S810A and QR312,313MG mutant GEF-H1S alleles constructed in the present invention. With respect to the latter allele, glutamine 312 and arginine at 313 of the GEF-H1S protein were mutated to methionine and glycine respectively, hence the designation, "QR312,313MG." Similarly, "S810A" indicates that serine residue at amino acid position 810 of the GEF-H1S protein was mutated to an alanine. Mutagenesis was performed by either PCR reaction or site directed mutagenesis.

| Amino acids | Alleles |
|---|---|
| 1-921 | wild type, S810A, QR312, 313MG, S67A |
| 1-386 | wild type |
| 386-921 | wild type |

-continued

| Amino acids | Alleles |
|---|---|
| 123-921 | wild type, S810A |
| 51-921 | wild type, S810A |
| 94-486 | wild type |

Oligonucleotides Used in Mutagenesis:

MC27 TGTAGATCCTCGGCGGCGCGCTCTC-CCCGCA (SEQ ID NO. 10). The "GCT" bolded residues denote a XhoII site, which changes the codon for Ser810 to Alanine. This was paired with MC3b and used in a PCR reaction creating a fragment which when restricted with XhoII and XhoI could be replaced with wild type cDNA fragment in the plasmid containing cDNA sequence coding for amino acids 386-921 (restricted with BamH1 and XhoI). The resulting newly constructed plasmid contained an alanine in position 810 of GEF-H1S. This mutant polypeptide was excised with Bcl1 and Xho1 and joined to a EcoR1 Bcl1 fragment which constitutes the remainder of gene making it full-length.

MC40 GGTGATGCCCATGGTCTCCAGCAGGAT (SEQ ID NO. 11) paired with MC1 and MC41 ATCCT-GCTGGTGACCATGGGCATCACCA (SEQ ID NO. 12) paired with MC3b were used in separate reactions to create overlapping fragments which could be joined by restricting with EcoR1, Nco1 and Xho1. MC40 and MC41 contain codons which produce the QR312,313MG mutant allele.

MC57 GCCGTGGCCGCTCCGCCTTGTCTTTA (SEQ ID NO. 13) and MC58 TAAAGACMGGCGGAGCGGC-CACGGC (SEQ ID NO. 14) were used in a site directed mutagenesis reaction (Stratagene Cat #200519, USA) which resulted in plasmid where an Alanine was placed in position 67. This reaction was performed in pBLUESCRIPT vector containing the fragment encoding the polypeptide 1-386. This piece was joined to the remainder of the GEF-H1 alleles (wild type, S810A, QR312,313MG) by restriction with EcoR1, Sac1 and Xho1.

Example 11

Analysis of GEF-H1S Alleles

Signal transduction involving the Rho family of GTPases is involved in a wide range of cellular responses, such as reorganization of the actin cytoskeleton, gene expression, apoptosis, membrane trafficking events, mitogenic signaling and malignant transformation. Typically, mutations within the highly conserved "QRITKY" (SEQ ID NO. 15) motif of the DH domain renders the protein incapable of binding the Rho GTPase protein and therefore enzymatically inactive.

In vitro transformation assays, according to the method of Clark et al, Methods Enzymol., 225:395-412, 1995, showed that wild type GEF-H1S is able to induce foci in NIH3T3 cells. Co-transformation assays between activated Ras with titrations of GEF-H1S wild type and GEF-H1S QR312, MG313 showed that GEF-H1S synergizes with activated Ras, however GEF-H1S QR312,MG313 inhibits foci formed by activated Ras.

Example 12

Localization and Morphological Changes

GEF-H1S alleles were transiently expressed in NIH3T3 cells or simultaneously expressed with PAK4 alleles. The GEF-H1S alleles were retrieved from the pcDNA vector by restriction with EcoR1 and Xho1 and inserted into pEGFP-C1 (Clontech, USA Cat #6082-1) restricted with EcoR1 and Sal1. The resulting protein was a hybrid of the brightly fluorescent protein, green fluorescent protein (GFP). The effects on cell morphology were traced by staining of F-actin with coumarin phallacidin (Molecular Probes, USA, Cat. #C-606). For experiments demonstrating co-localization with PAK4, PAK4 was in the pcDNA expression vector with either a myc or HA affinity tag and is detected by the monoclonal antibody, "9E10" or "HA7," sandwiched with goat anti-mouse linked with rhodamine (Santa Cruz, USA) which fluoresces red. Wild type GEF-H1S was localized at the perinuclear region of the Golgi apparatus. See, Callow et al., 2002. This finding was consistent with GEF-H1S being a substrate for PAK4, because activated PAK4 is also localized to the Golgi apparatus.

The phosphorylation mutant S810A, however, was localized to the cytoplasm, indicating that phosphorylation of S810 is important for localization of GEF-H1S. The DH mutant QR312,MG313 was also found to be localized in the cytoplasm and displayed a staining pattern of cytoplasmic aggregates. These observations were specific for GEF-H1S alleles since GFP itself did not localize to any similar cellular compartments.

Expression of the PAK4 wild type allele simultaneously with the GEF-H1S wild type allele in NIH3T3 cells induced formation of peripheral actin microspikes similar to those attributed to overexpression of the Rho GTPase Cdc42. This suggests an important role for both PAK4 and GEF-H1S in the formation of these structures. Simultaneous expression of activated PAK4 S474E and GEF-H1S caused the formation of lamellipodia which further implicate PAK4 and GEF-H1S as a complex of proteins that are involved in RhoGTPase signaling. See, Nobes et al., *Biochem Soc Trans.*, 23(3):456-9, 1995. These actin-based morphologies were specific to the combined PAK4 kinase and GEF-H1 exchange activity, because there was no actin-based structures when inactive kinase was expressed with wild type GEF-H1. Similarly the combination of PAK4 and the exchange factor inactive mutant prevented the formation of actin based structures.

Example 13

This example contains additional information about certain methods described herein.

Cloning of GEF-H1

Plasmid pGEX-4T (Amersham Biosciences Cat #27-4581-01) expressing a polypeptide of the catalytic domain of PAK4 (amino acids 291-591) was used as a bait in a phage display screen for protein interactors. The phage display library was derived from the breast tumour line MCF-7. Sequences from the phage plasmids were used to query the database at the National Centre for Biotechnology (NCBI) using Basic Local Alignment Search Tool (BLAST). Two of the cDNAs matched >99% identity with the cDNA denoted KIAA0651 (Genbank accession number: AB014551) and several overlapping expressed sequence tags (ESTs). During cloning of GEF-H1 it was found that the gene had three major splice isoforms, GEF-H1M, GEF-H1S and GEF-H1U. The GEF-H1S (amino acids 1-921) isoform differs from GEF-H1M splice-forms due to a mini-exon of 7 amino acids as well as the lack of the exon that encodes for the N-terminal zinc finger domain. The splice-form referred to as GEF-H1M contains the zinc finger region involved in microtubule binding and is identical to the full length version (aa1-985) referred to as GEF-H1. In-frame sequences were subcloned into pGEX-4T for substrate analysis.

DNA Plasmids and Constructs

To obtain GEF-H1S, the oligonucleotides MC1 GCAG-MTTCTGTAACAAGAGCATCACA (SEQ ID NO: 16) and MC3b GCGCTCGAGTTAGCTCTCGGAGGCTA-CAGCCT (SEQ ID NO: 17), derived from sequence KIAA0651, were used in 20 rounds of Polymerase Chain Reaction (PCR) to amplify the gene from a human whole brain plasmid cDNA library (CLONTECH laboratories Cat #HL9002CC). A ~3000 bp fragment was obtained, subcloned and three clones sequenced yielding identical results. An EcoR1-Xho1 was used for subcloning in frame into a pcDNA vector harbouring the HA-epitope 5' to the MCS. EcoR1-Xho 1 fragment from pcDNA clones were used for shuttling all GEF-H1 alleles to in frame Eco-R1-Sal 1 digested pEGFPC (Clontech) respectively.

Mutant S810A was introduced by PCR reaction with oligos MC27 TGTAGATCCTCGGCGGCGCGCTCTC-CCCGCA (SEQ ID NO: 10) and MC3b. The mutant insert was introduced to a deletion mutant of GEF-H1S spanning nucleotides 1100-2761 and wild type BamH1-Xho1 fragment was substituted with mutant XhoII and XhoI fragment. Oligonucleotides MC40 GGTGATGCCCATGGTCTC-CAGCAGGAT (SEQ ID NO: 11), MC1, MC 41 ATCCT-GCTGGTGACCATGGGCATCACCA (SEQ ID NO: 12) and MC3b were used to create overlapping EcoR1-Nco1 and Nco1-Xho1 fragments to convert QR residues to MG in the highly conserved QRITY motif of the DH domain. S67A was created using oligos MC57 GCCGTGGCCGCTCCGCCT-TGTCTTTA (SEQ ID NO: 13) and MC58 TAAAGACAAG-GCGGAGCGGCCACGGC (SEQ ID NO: 14) and pBluescipt GEF-H1S spanning 1-626 as a backbone in a site directed mutagenesis reaction (Stratagene). This mutant fragment was digested with EcoR1-Sac1 and joined to the remainder of the gene with a Sac-Xho1 generated fragment from mutant and wild type alleles. Since GEF-H1M and S proteins differ only in their amino termini it was generated as a hybrid by joining mutant and wild type sequences derived from GEF-H1S. The unique 5' sequence was generated with the oligonucleotides MC61 GCGGAATTCATGTCTCG-GATCGAATCCCTCA (SEQ ID NO: 26) and MC62 GTCACTGAGCTCGTCCACGCAGGGGA (SEQ ID NO: 27) in a PCR reaction using IMAGE clone 4157775 (Research genetics) as a template.

Preparation of Recombinant Proteins, Sequence of Peptides and Kinase Assays

Glutathione-s-transferase (GST) fused PAK4 (residues 291-591), GEF-H1 amino acids 763-921 (from phage clone 13.8 sequence, matches KIAA0651) and Maguin 2-like (from phage clone 13.32, sequence matches accession #XP-087831) were purified by standard procedures and as previously described 31. Amino acid sequence of peptides spanning GEF-H1b 807-824 #1008 (RRRSLPAGDALYLpSFNPP) (SEQ ID NO: 28), #1009 (RRRpSLPAGDALYLSFNPP) (SEQ ID NO: 29), #1010 (RRRSLPAGDALpYLSFNPP) (SEQ ID NO: 30) and #934 (RRRSLPAGDALYLSFNPP) (SEQ ID NO: 3) used for in vitro kinase assays. In vitro kinase reactions were run as described previously 31.

Antibodies and Immunoreagents

KLH linked peptide (#1009) CRRRSLPAGDALYLS-FNPP (SEQ ID NO: 52) (residues 807-824) with a phosphorylated serine in position 810 and (#104) GST-GEF-H1 (residues 762-921) were used as antigens to raise anti-serum in rabbits. PAK4 antibodies were derived from the antigens (#933) CATTARGGPGKAGSRGRFAGHSEA (SEQ ID NO: 31) (residues 122-144) and (#80) CSGDRRRAGPEKRPKSS (SEQ ID NO: 23) (residues 148-163). Specificity was analysed as described previously. Goat anti-mouse and anti-rabbit IgG horseradish peroxidase conjugates were from Roche molecular. Goat anti-mouse and anti-rabbit linked to fluorophores FITC or rhodamine were from Santa Cruz biotechnology and Mouse anti-tubulin was from Zymed. Coumarin-phallicidin and Phalloidin-FITC were from molecular probes. Mouse anti-cascade blue and the fluorescent dyes; Texas red, FITC or marina blue were obtained and conjugated to antibodies according to the manufacturer. The solutions of cross-linking reagent were quenched by desalting through G25 sephadex and mixing with ammonium chloride to a final concentration of 50 mM.

Cell Transfections and Immunofluorescence

NIH-3T3, 293T, A549, HCT116 and H1299 cells were maintained in Dulbecco's modified Eagles medium (DMEM) 10% Fetal Bovine serum (FBS), penicillin and streptomycin from Invitrogen (Carlsbad, Calif.). For transfection, cells were seeded at 105 cells ml-1 for NIH-3T3 and 104 cells ml-1 for both 293T and H1299 unless otherwise stated. Transfection reagents Lipofectamine 2000 (Invitrogen) or Fugene (Roche Molecular) were used at 3 µg µg$^{-1}$ of plasmid DNA. Cellular extracts for immunoblotting were prepared in lysis buffer. For immunoprecipitation experiments lysates were incubated with Protein G beads (Pharmacia) linked with appropriate antibody, glutathione sepharose beads (Pharmacia) with appropriate GST fusion protein and streptavidin beads (Pierce) linked to appropriate biotinylated peptides. For immunofluorescence, coverslips were placed in 24 well cell culture vessels and seeded at the densities above. Transfections took place after 16 h and unless otherwise stated were maintained in Optimem or DMEM with 0.2% FBS for 24 h until fixation. Microscopy was performed on a Nikon E800 microscope with 60× objective (1.5 NA). Images were captured with a CCD SPOT camera and pseudo-coloured with SPOT imaging software (Diagnostic instruments).

Example 14

Measuring PAK4 Kinase Activity in Whole Cells Using ELISA

The level of PAK4-dependent phosphorylation of GEF-H1S can be determined by monitoring the binding of a phosphospecific antibody to GEF-H1S according to the following protocol. ELISA plates (Corning, 96 well plates, Cat. #25805-96) were pre-coated with anti-HA monoclonal antibody at 5 µg/ml in PBS, using 100 µl final volume per well and stored overnight at 4° C. The coating buffer was then removed and replaced with blocking buffer (2% BSA in TBST) and the entire plate then shaken at room temperature for 60 minutes.

Tissue culture plates were then coated with poly-L-lysine, using 50 µl per well and then incubated at 37° C. for 30 minutes. The plates were then rinsed with PBS, extra liquid aspirated off and allowed to dry fully before use. When dry, TR-293-KDG cells were seeded into each well at 2×10$^{+4}$ cells per well in a 100 µl volume of DMEM and 10% Clontech-approved FBS, and left to incubate at room temperature for at least 2 hours. At that time, the medium was removed and replaced with 100 µl of low-serum medium (DMEM, 0.2% BSA and 1% Clontech-approved FBS), that was supplemented with 1 µg/ml of doxycycline. The negative control wells were not treated with doxycycline.

The next day, candidate substances were diluted as required in a solution containing 0.2% BSA, 10 mM HEPES and 1 µg/ml of doxycycline. A candidate substance were diluted by first preparing a 10 mM stock of the substance in 100% DMSO. 5 µl of that solution was then added to 15 µl of DMSO to prepare a 2.5 mM (50× concentration) solution. 6 µl of this final solution was then transferred to a well of a polypropylene plate, to which 300 µl of medium was added. 100 µl of the solution in the well was then added to each well containing cells, by removing the medium coating the cells and the solution containing the dilutions of the candidate substance gently added.

Fresh HNTG$^{plus}$ solution was then prepared by adding 1 tablet of "complete mini" protease inhibitor cocktail (Roche) to 10 ml water, 200 µl of β-glycerophosphate (final concentration, 1M), 100 µl of NaF (final concentration, 1M), and 10 µl of Na$_3$VO$_4$ (final concentration, 1M) and kept on ice. After the cells had been incubating for 3 hours with the diluted candidate substance, the medium was removed and the plate transferred onto ice. 100 µl of the fresh HNTG$^{plus}$ solution was then added to each well containing cells and shaken in a cold room for 10 minutes. During this time, the BSA from the ELISA plates was pipetted off and washed twice with TBST.

50 µl of a cell lysate was then transferred from the tissue culture plate to a washed well of the ELISA plate and shaken at room temperature for 60 minutes. Then, the cell lysate was removed and the wells of the ELISA plate washed three times with TBST. 100 µl of freshly-diluted anti-pGEF antibody (1:5000) was then transferred to each well of the ELISA plate and shaken at room temperature for 60 minutes. The antibody solution was removed and the wells washed four times with TBST. Then, 100 µl of freshly-diluted HRP-GaR (1:10,000) was added to each well of the ELISA plate and shaken at room temperature for 45 minutes. This solution was then removed and the wells washed four times with TBST, followed by one wash with PBS. ABTS solution was then added to the plate at 100 µl per well. The ELISA plate was then incubated at room temperature and shaken for between 10 and 20 minutes.

After that time, the ELISA plate was placed onto a Tecan Sunrise plate reader and measurements recorded using a measurement filter 405 nm with a reference filter of 620 nm.

Example 15

Measuring the In Vitro Kinase Activity of Human PAK4 Using a Scintillation Proximity Assay The Scintillation Proximity Assay (SPA) is used to analyze protein serine/threonine kinase activity of PAK4 in vitro. The protocol involved adding 10 µl of inhibitor solution to each well of a flexiplate (Wallac 96-well polyethylene terephthalate ("flexi") plate, Cat. #1450-401), using 10 µl of 5% DMSO for positive and negative controls.

PAK4 enzyme was added to the wells of the flexiplate at concentrations that were determined empirically. PAK4 enzyme was purified from BL21 cells. At the time of this experiment, the concentration of PAK4 kinase enzyme added to the wells was 0.1 µg per well in a volume of 20 µl. The concentration will vary with various preparations of enzyme. Accordingly, the skilled artisan would know how to titrate the enzyme preparation and determine a timecourse of linear kinase activity for particular preparations of the kinase. 20 µl of 0.5M EDTA is added to the negative control wells. The substrate was a PAK4 peptide that is known to be phosphorylated by PAK enzyme, consisting of the structure,

```
biotin-LC-LC-RRKSLVG(pT)PYWMAPE    (SEQ ID NO. 19)
```

The eighth amino acid of the PAK4 peptide, threonine, was a phosphothreonine, and the entire peptide was dissolved in water to a final concentration of 5 mg/ml and stored at −80° C.

in 100 µl aliquots until needed. However, the invention contemplates that any peptide that is believed to be, or is, phosphorylated as a substrate by PAK kinase (e.g. PAK4) can be used instead of the PAK4 peptide. For instance, the GEF-H1S peptides represented by SEQ ID NOs. 3 and 4 can be used as a PAK4 substrate.

2.5× kinase buffer was used to facilitate PAK4 kinase activity and contained working concentrations per well of 50 mM HEPES (pH 7.4), 12.5 mM of $MgCl_2$, 375 mM KCl and 2.5 mM NaF. Typically, 10 ml of kinase buffer is sufficient for approximately 4.5 plates of reactions. The final concentrations of these constituents, following additions of candidate substance and ATP, are 20 mM HEPES (pH 7.4), 5 mM $MgCl_2$, 150 mM KCl and 1.0 mM NaF.

To start the kinase reaction, 20 µl of PAK4 biotinylated peptide/ATP solution was added to the wells of the plate and incubated at room temperature for 30 minutes, without shaking, and positioned behind a reactive shield. The peptide/ATP solution contained working concentrations (i.e., concentrations per well) of 1.4 µM cold (i.e., non-radioactive) ATP, 0.1 µg per well of Paktide and 0.33 µCi per well of radiolabelled, $γ^{33}P$-ATP (NEN Easy-Tide, Cat. #NEG602H). After 30 minutes, 200 µl of stop solution was added to each well and the plate allowed to stand for at least 15 minutes. "Stop" solution contained working concentrations per well of 50 µM ATP (unlabeled), 5 mM EDTA, 0.1% Triton X-100 and 0.5 mg of SPA beads, made up in PBS buffer solution. PBS (Dulbecco's Phosphate-Buffered Saline) without magnesium or calcium was obtained from Gibco BRL (Cat. #14190-144). The beads were obtained from Amersham (Amersham streptavidin-coated polyvinyltoluene SPA beads, Cat. #NIF 1077). The beads were reconstituted in PBS without magnesium or calcium to a stock concentration of 20 mg/ml and stored at 4° C.

The plate was then centrifuged/spun at 2300 rpm for between 10 and 15 minutes and then transferred to a Trilux plate reader and the radioactivity counts recorded accordingly.

Example 17

Induction of the Serum Response Element

Activation of the transcription factors which converge on the serum response element (SRE) can be attributed to Ras activation, which is observed in as many as 50% human colon carcinomas. See, Gauthier-Rouviere et al., *Embo J.*, 9(1):171-80, 1990.

Signaling to the SRE by GEF-H1S and PAK4 activity downstream of ras and rho proteins was determined by using a pSRE-SEAP vector system (Clontech, USA). This assay was performed in NIH3T3 cells using standard transfection methods. The inactive GEF-H1S allele, QR312,313MG, reduced levels of activated rac RhoGTPase in stimulated cells. See, Taylor et al., *Methods Enzymol.*, 333:333-42, 2001.

Furthermore, signaling to SRE is reduced almost to basal levels by transient expression of the inactive mutant allele GEF-H1S QR312,313MG and phosphorylation mutant S810A.

Example 18

Morphological Changes Mediated by GEF-H1 Alleles

To analyse the effect of GEF-H1 on cell morphology in fibroblasts, EGFP (enhanced green fluorescent protein) fusion constructs of GEF-HIS and a series of mutant alleles of the PAK4 phosphorylation sites in GEF-HIS were transfected into NIH3T3 cells. Also constructed was a dominant negative allele, made by mutating the DH domain of GEF-H1, which produced the mutant, GEF-H-QR3I2,313MG. In a p21-binding domain (PBD) assay this dominant-negative allele inhibited accumulation of Rac-GTP but not Cdc42-GTP in Nlli-3T3 cells. The actin cytoskeleton was stained with coumarin-phallicidin to contrast F-actin structures of EGFP fluorescing cells by microscopy.

It was found that wild type GEF-H1S typically localized to the perinuclear region and cells appeared elongated with occasional stress fibres. By contrast over-expression of GEF-H1S-S8I0A alone lead to an accumulation and disorganized array of stress fibres compared to non-transfected cells. The induction of stress fibres is striking given the relatively modest effects on the actin cytoskeleton upon expression of either wild type GEF-HIS or PAK4 alleles alone. The morphology of GEF-HIS-S67A expressing cells was similar to the morphology of cells expressing the dominant negative GEF-H1S DH mutant.

Expression of the DH domain mutant GEF-HIS-QR312,313MG, creates a trail of wildly distributed cytoplasmic extensions. The induction of stress fibres in the case of GEF-HIS-S810A is reminiscent of Rho activation, while the disorganized cytoplasmic extensions seen with GEF-HI-Q312R, M313G and GEF-H1S-S67A could be remnants of non-retracted cell tails that might be due to Rho inhibition.

The changes in localization and the actin cytoskeleton is especially dramatic in the double mutant of GEF-H1S-(S67A-S810A). Cytoplasmic aggregates of F-actin were found in EGFP-GEF-HIS (S67A-S810A) expressing cells, as well as wide-arcing lamella devoid of F-actin. The redistribution of the phosphorylation-site mutant proteins and inappropriate accumulation of cytoplasmic F-actin, supports the idea that localization is critical for the ability of GEF-H1 to stimulate stress fibres.

Example 19

Activated PAK4 and GEF-HIS Induce Lamellipodia Formation in NIH-3T3 Cells

Induction of F-actin structures in fibroblasts, namely the formation of filopodia, lamellipodia, and stress fibres is due to signalling by the active forms of Cdc42, Rac, and Rho, respectively. PAK proteins, especially PAK4, play a role in regulating F-actin based morphological structures. Accordingly, PAK4-induced changes in cell morphology, mediated by regulation of GEF-HIS, were investigated. EGFP-GEF-HI constructs were co-expressed with various HA epitope-tagged PAK4 alleles in NIH3T3 cells. Exogenous PAK4 was detected with an anti-HA antibody and the actin cytoskeleton was stained with coumarin phallicidin. Although NIH-3T3 cells have low but detectable levels of endogenous PAK4 and GEF-HI, these were not activated under the conditions of the experiment.

By employing various alleles of PAK4, it was possible to confirm which morphological effects were driven through PAK4 phosphorylation of GEF-H1. Co-expressing the PAK4 alleles with the EGFP control produced relatively modest effects on the formation of F-actin based structures in NIH3T3 cells. In cells co-expressing wild-type PAK4 together with wild type GEF-HIS, we observed a dramatic increase in filopodia in contrast to either PAK4 or GEF-H1S expressed alone. The filopodial structures seemed to be dependent on the lower activity of the wild type PAK4 allele and the interaction with GEF-H1S since they were not observed when either protein was expressed in cells alone or in vector co-transfected controls. In cells co-expressing the activated PAK4 S474E and GEF-HIS, these structures transitioned from filopodia to lammellipodia at the leading edge. Neither filopodia nor lammellipodia were observed when GEF-HIS was transfected together with the kinase inactive PAK4 K350,351A however stress fibres were now abundantly present. Taken together with the analysis of the rAK4 phosphorylation site mutants in GEF-HIS, this suggests that PAK4 kinase activity is responsible for the transition to lamellipodia formation.

To confirm whether the formation of these structures is dependent on the ability of PAK4 to phosphorylate GEF-HIS, phosphorylation site mutants of GEF-H1S were utilized. Co-transfection of a mutant GEF-H1S-S810A allele together with PAK4 S474E shows a profusion of stress. This together with the result from the kinase-dead allele prompted the hypothesis that phosphorylation of Ser 810 is responsible for both the signals that lead to lamellipodia formation, and for the inhibition of stress fibre formation in fibroblasts. Additionally PAK4 S474E and GEF-H1S S810A localized to distinct peripheral sites reminiscent of cell adhesion attachment sites that serve as nucleation points for actin stress fibres. This type of localization of GEF-HI has also been seen in HeLa cells. Conversely to the effects seen by mutation of 5810, co-expression of mutant GEF-H1 S-S67 A with activated PAK4-S474E allows GEF-H1 dependent formation of lamellipodia while preventing stress fibre formation.

Exchange activity of GEF-HI is achieved through the interaction of the Dbl homology (DH) domain with the Rac or Rho GTPases in their inactive state. To determine whether GEF-HIS mediated effects driven by PAK4 phosphorylation are dependent upon GEF-HIS exchange activity NIH-3T3 cells co-expressing the GEF-H1S dominant negative DH mutant (Q3I2M,R3I3G) with various alleles of PAK4, were examined. Consequently, wide-arcing lamella lacking actin were observed, which is in contrast to the actin rich lamellipodia or stress fibres formed in the presence of active alleles of GEF-HIS and activated PAK4. The result confirms that PAK4 signals are relayed directly through the exchange activities of GEF-HI. A previous study of GEF-H1 showed constitutive lamellipodia induction in Cos-7 cells by overexpression of GEF-HI14.

What is claimed is:

1. A method for detecting PAK4 activity in a cell sample in vitro, comprising detecting the presence or level of phosphorylated GEF-H1 using a GEF-H1-phophospecific antibody, wherein the phosphorylation site of the GEF-H1 corresponds to the serine-810 of SEQ ID NO:2, wherein the GEF-H1-phosphospecific antibody specifically binds to a peptide comprising the amino acid sequence of SEQ ID NO:3, wherein the serine at position 4 of SEQ ID NO:3 is phosphorylated, and wherein the detection of phosphorylated GEF-H1 indicates the presence of at least one active PAK4.

2. The method of claim 1, wherein the cell is a tumor cell.

3. The method of claim 2, wherein the tumor cell is collected from a mammal.

4. The method of claim 3, wherein the mammal is selected from the group consisting of a human, rat, mouse, dog, rabbit, pig, sheep, cow, horse, cat, primate, goat, and monkey.

5. A method for determining the presence of activated PAK4 in a cell sample comprising:

(a) obtaining a cellular lysate from the cell sample;

(b) isolating and/or separating proteins from the cell lysate preparation; and (c) detecting the presence of phosphorylated GEF-H1 using a GEF-H1-phosphospecific antibody, wherein the phosphorylation site of the GEF-H1 corresponds to the serine-810 of SEQ ID NO:2, wherein the GEF-H1-phosphospecific antibody specifically binds to a peptide comprising the amino acid sequence of SEQ ID NO:3, wherein the serine at position 4 of SEQ ID NO:3 is phosphorylated, and wherein detecting the presence of phosphorylated GEF-H1 indicates that the cell sample comprises activated PAK4.

6. The method of claim 5, wherein the cell sample is a tumor cell sample.

* * * * *